US006550304B2

United States Patent
Lloyd et al.

(10) Patent No.: US 6,550,304 B2
(45) Date of Patent: Apr. 22, 2003

(54) METHOD OF COMPENSATING A MOS GAS SENSOR, METHOD OF MANUFACTURING A MOS GAS SENSOR, MOS GAS SENSOR, AND FUEL CELL SYSTEM

(75) Inventors: Greg A. Lloyd, Spokane, WA (US); William A. Fuglevand, Spokane, WA (US)

(73) Assignee: Avista Laboratories, Inc., Spokane, WA (US)

( * ) Notice: Subject to any disclaimer, the term of this patent is extended or adjusted under 35 U.S.C. 154(b) by 0 days.

(21) Appl. No.: 10/187,707

(22) Filed: Jul. 1, 2002

(65) Prior Publication Data

US 2003/0019275 A1 Jan. 30, 2003

Related U.S. Application Data

(62) Division of application No. 09/916,850, filed on Jul. 26, 2001.

(51) Int. Cl.[7] .......................... G01N 21/00; G01N 19/10
(52) U.S. Cl. .......................................... 73/1.02; 73/23.2
(58) Field of Search ..................... 73/23.2, 23.21, 73/31.06, 1.06; 422/98

(56) References Cited

U.S. PATENT DOCUMENTS

| 3,498,844 A | 3/1970 | Sanderson |
| 3,507,702 A | 4/1970 | Sanderson |
| 3,528,858 A | 9/1970 | Hodgdon, Jr. et al. |

(List continued on next page.)

FOREIGN PATENT DOCUMENTS

| EP | 1 111 703 A2 | 6/2001 | |
| JP | 60-88356 | 5/1985 | .......... G01N/27/12 |
| JP | 02002071611 | 8/2002 | .......... G01N/27/12 |

OTHER PUBLICATIONS

U.S. patent application Ser. No. 09/322,666, Fuglevand et al., filed May 28, 1999.

U.S. patent application Ser. No. 09/577,407, Fuglevand et al., filed May 17, 2000.

*Primary Examiner*—Helen Kwok
*Assistant Examiner*—Jay L Politzer
(74) *Attorney, Agent, or Firm*—Wells St. John P.S.

(57) ABSTRACT

A method of compensating a MOS gas sensor is described and which includes using a MOS gas sensor to provide a signal indicative of gas concentration of a target gas in an ambient; providing a signal representative of dew point of the ambient; and modifying the signal from the MOS gas sensor using the signal representative of dew point to simultaneously compensate for the effects of both temperature and relative humidity on the MOS gas sensor.

5 Claims, 16 Drawing Sheets

U.S. PATENT DOCUMENTS

| | | | |
|---|---|---|---|
| 3,623,913 A | 11/1971 | Adlhart et al. | |
| 3,964,930 A | 6/1976 | Reiser | |
| 3,969,145 A | 7/1976 | Grevstad et al. | |
| 4,117,082 A | 9/1978 | Matsuyama | |
| 4,192,906 A | 3/1980 | Maru | |
| 4,276,355 A | 6/1981 | Kothmann et al. | |
| 4,313,338 A | 2/1982 | Abe et al. | |
| 4,459,577 A | 7/1984 | Murakami et al. | |
| 4,469,579 A | 9/1984 | Covitch et al. | |
| 4,575,441 A | 3/1986 | Murakami et al. | |
| 4,624,137 A | 11/1986 | Johnson et al. | |
| 4,658,632 A | 4/1987 | Sasaki | |
| 4,661,411 A | 4/1987 | Martin | |
| 4,701,739 A | 10/1987 | Sasaki | |
| 4,718,991 A | 1/1988 | Yamazoe et al. | |
| 4,731,226 A | 3/1988 | Takahata et al. | |
| 4,769,297 A | 9/1988 | Reiser et al. | |
| 4,795,536 A | 1/1989 | Young et al. | |
| 4,795,683 A | 1/1989 | McElroy | |
| 4,797,185 A | 1/1989 | Polak et al. | |
| 4,801,211 A | 1/1989 | Yagi et al. | |
| 4,816,800 A | 3/1989 | Onaga et al. | |
| 4,818,637 A | 4/1989 | Molter et al. | |
| 4,826,741 A | 5/1989 | Aldhart et al. | |
| 4,826,742 A | 5/1989 | Reiser | |
| 4,827,154 A | 5/1989 | Naoyuki et al. | |
| 4,876,115 A | 10/1989 | Raistrick | |
| 4,938,928 A | 7/1990 | Koda et al. | |
| 4,958,513 A | 9/1990 | Yasunaga et al. | |
| 4,988,582 A | 1/1991 | Dyer | |
| 5,006,828 A | 4/1991 | Yutaka et al. | |
| 5,066,466 A | 11/1991 | Holter et al. | 422/98 |
| 5,084,144 A | 1/1992 | Reddy et al. | |
| 5,132,193 A | 7/1992 | Reddy et al. | |
| 5,242,764 A | 9/1993 | Dhar | |
| 5,318,863 A | 6/1994 | Dhar | |
| 5,507,175 A | 4/1996 | Cooper | |
| 5,716,506 A | 2/1998 | Maclay et al. | |
| 5,719,778 A | 2/1998 | Suzumura et al. | |
| 5,739,416 A | 4/1998 | Hoenk | |
| 5,759,367 A | 6/1998 | Matsuura et al. | |
| 5,814,970 A | 9/1998 | Schmidt | |
| 5,821,729 A | 10/1998 | Schmidt et al. | |
| 5,918,261 A | 6/1999 | Williams et al. | |
| 5,969,231 A | 10/1999 | Qu et al. | |
| 6,001,499 A | 12/1999 | Grot et al. | |
| 6,030,718 A | 2/2000 | Fuglevand et al. | |
| 6,096,449 A | 8/2000 | Fuglevand et al. | |
| 6,126,311 A | 10/2000 | Schuh | |
| 6,155,098 A | 12/2000 | Shapiro et al. | |
| 6,387,556 B1 | 5/2002 | Fuglevand et al. | |
| 2001/0045118 A1 | 11/2001 | Lloyd et al. | 73/1.06 |
| 2001/0053465 A1 | 12/2001 | Fuglevand | 429/9 |

METHOD OF COMPENSATING A MOS GAS SENSOR, METHOD OF MANUFACTURING A MOS GAS SENSOR, MOS GAS SENSOR, AND FUEL CELL SYSTEM

CROSS REFERENCE TO RELATED APPLICATION

This is a Divisional of U.S. patent application Ser. No. 09/916,850, filed Jul. 26, 2001, and titled "Method of Compensating a MOS Gas Sensor, Method of Manufacturing a MOS Gas Sensor, MOS Gas Sensor, and Fuel Cell System".

TECHNICAL FIELD

The present invention relates to gas sensing instruments, and more specifically to compensating gas sensors for the effects of ambient conditions such as temperature and humidity. The present invention also relates to metal oxide semiconductor sensors utilized as gas sensors.

BACKGROUND OF THE INVENTION

For safety purposes, gas-sensing instruments are used in many industrial applications such as in fuel cell systems whose feedstocks are flammable gases. It is well known that many gas sensors—metal oxide semiconductor (MOS) based sensors in particular—suffer from environmental dependencies. That is, ambient temperature and relative humidity substantially affect their sensitivity. For example, one commercially available MOS sensor model is the Figaro TGS821 hydrogen sensor. Due to the combination of this sensor's environmental dependencies and the environmental uncertainties to which it will be exposed to in certain fuel cell applications, a sensor reporting a reading of 526 PPM of hydrogen might actually be exposed to a true concentration ranging between 182 and 1627 PPM. In certain fuel cell applications, the lower reading would be regarded as being well below alarm-level whereas the higher reading would be regarded as being well above. This 8.9:1 range of uncertainty is the source of much frustration with uncompensated MOS gas sensors.

Accordingly, many designers of gas sensing instruments elect to compensate for MOS gas sensors' environmental dependencies. The conventional wisdom is that this requires a microprocessor, firmware (software), and lookup charts. However, dependence upon firmware being perpetually executed without error in a microprocessor-based circuit greatly complicates efforts to design a highly reliable, fail-safe gas-sensing instrument. Furthermore, the conventional method produces compensation factors that are inexact approximations of the required values.

Attention is invited to the following U.S. patents, which are incorporated herein by reference: U.S. Pat. Nos. 5,716,506 to Maclay et al.; 4,313,338 to Abe et al.; 4,801,211 to Yagi et al.; 6,126,311 to Schuh; and 5,969,231 to Qu et al.

U.S. Pat. No. 5,716,506 to Maclay et al. discloses (see Col. 1) a gas sensor that compensates for relative humidity and temperature of the air in the detection of a predetermined gas in a microfabricated electrochemical sensor.

U.S. Pat. No. 4,313,338 to Abe et al. relates to a gas sensing device comprising a resistive film formed of ultra fine particles of a metal oxide (Col. 4, lines 10–15). The gas sensing device includes (Col. 7, line 43-Col 8, line 65) a temperature sensing element for maintaining the temperature of the gas sensitive element constant. U.S. Pat. No. 4,313,338 also discloses obviating the problem of water vapor obstructing the successful measurement of the concentration of gas by using a single gas sensing element to sense both the concentration of water vapor and the concentration of isobutane gas (see Col. 8, line 47-Col. 9, line 11). The gas sensing element is heated up 300 degrees Celsius during the measurement of the concentration of the isobutane gas and is cooled down to the room temperature of 25 degrees C. during the measurement of relative humidity.

U.S. Pat. No. 4,801,211 to Yagi et al. discloses (see Abstract) a humidity sensor that, when temperature corrected, indicates a dew point at a fixed temperature. By adjusting this fixed temperature dew point output according to a sensed temperature, the dew point can be detected. FIG. 2 shows analog circuitry employed with same. The sensor is fabricated from metal oxide ceramic material (see Col. 4, lines 44–46).

U.S. Pat. No. 6,126,311 to Schuh discloses (see FIG. 4) a sensor that outputs dew point, ambient temperature, and relative humidity. This patent discloses (see Col. 1, lines 14–20) that the relative humidity and dew point of a gaseous sample are closely related by well known algorithms for converting dew point and ambient temperature to relative humidity or converting relative humidity and ambient temperature to dew point. This patent also indicates (see Col. 2, lines 19–23) that a group of prior art sensors measure the relative humidity of an ambient environment as opposed to dew point, and that relative humidity and dew point are easily converted from one to the other with a measurement of the ambient air temperature.

U.S. Pat. No. 5,969,231 to Qu et al. discloses a sensor for monitoring the concentration of moisture and gaseous substances in the air. Semiconductive metal oxides are used (see Col. 1).

Notwithstanding the prior art teachings noted above, none of these references singularly or in any permissible combination teach a simple approach for compensating gas sensor measurements for both humidity and temperature at the same time. It would be advantageous therefore, to be able to perform such compensation utilizing analog circuitry, which would be highly reliable and fail safe.

Gas sensors are used, in various industrial applications, such as in the fabrication of fuel cells. For example, gas sensors configured to sense hydrogen can be employed to detect hydrogen fuel leaks or hydrogen fuel flow in the fuel cells. In this regard, attention is directed to commonly assigned U.S. patent application Ser. No. 09/322,666 filed May 28, 1999, listing as inventors Fuglevand et al., and which is incorporated by reference herein. This application discloses the particulars of how gas sensors can be employed in one form of a fuel cell system.

BRIEF DESCRIPTION OF THE DRAWINGS

Preferred embodiments of the invention are described below with reference to the following accompanying drawings.

DETAILED DESCRIPTION OF THE PREFERRED EMBODIMENTS

Figure 1:
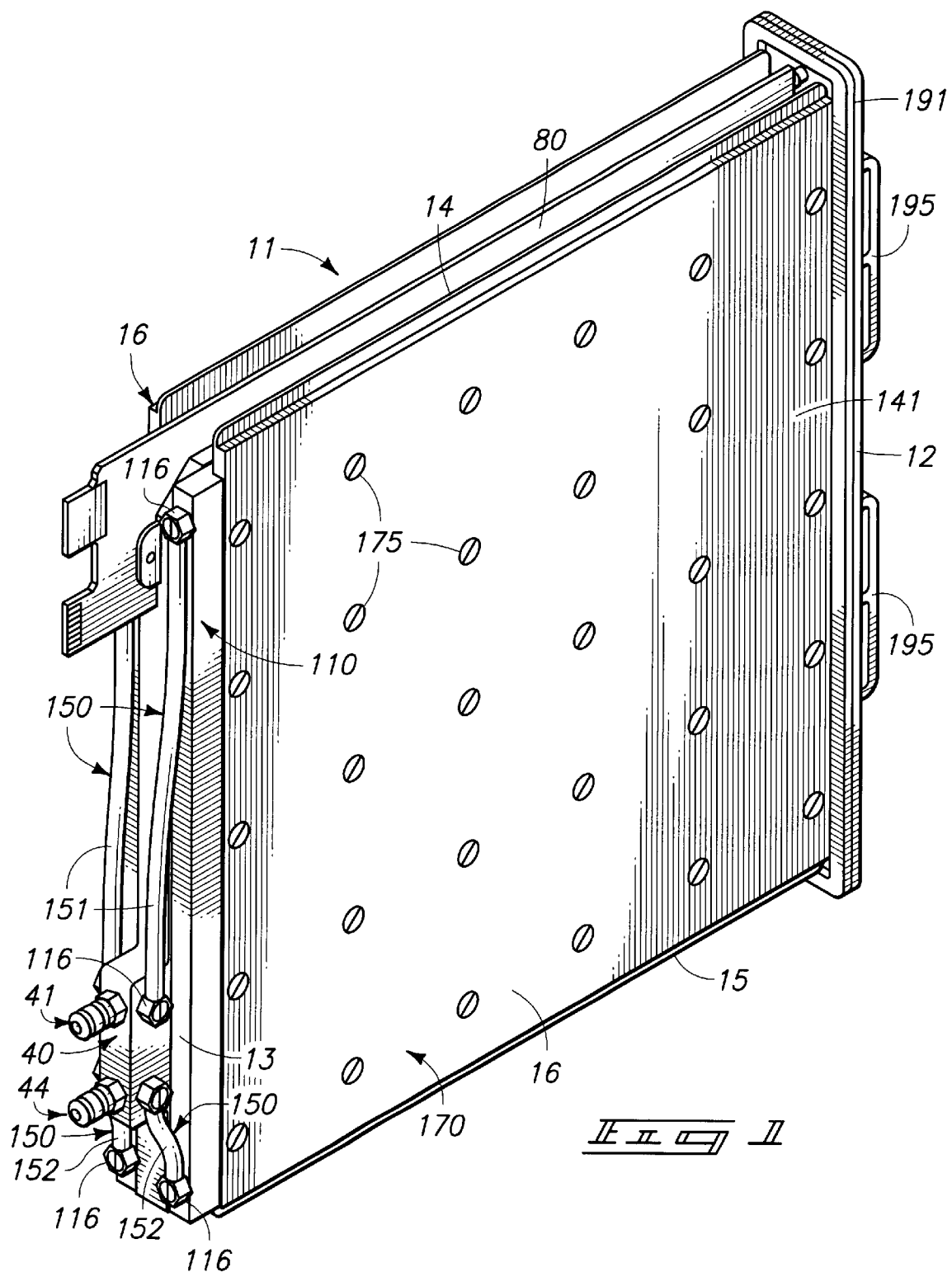
FIG. 1 is a perspective, side elevation view of an ion exchange membrane fuel cell module which is utilized with a fuel cell power system embodying the present invention.

This disclosure of the invention is submitted in furtherance of the constitutional purposes of the U.S. Patent Laws "to promote the progress of science and useful arts" (Article 1, Section 8).

The present invention provides for a method of compensating a MOS gas sensor, comprising using a MOS gas sensor to provide a signal indicative of gas concentration of a target gas in an ambient; providing a signal representative of dew point of the ambient; and modifying the signal from the MOS gas sensor using the signal representative of dew point to simultaneously compensate for the effects of both temperature and relative humidity on the MOS gas sensor.

Another aspect of the present invention provides for a method of compensating a MOS gas sensor, comprising: utilizing a MOS gas sensor, providing a signal indicative of gas concentration of a target gas in an ambient; determining the dew point of the ambient; determining a compensation factor for the MOS gas sensor, the compensation factor being determined based upon the ascertained dew point; and modifying the resulting signal from the MOS gas sensor using the compensation factor.

Another aspect of the present invention provides for a MOS gas sensor system comprising a MOS gas sensor configured to provide a signal indicative of gas concentration of a target gas in an ambient; equipment configured to determine the dew point of the ambient; and compensation circuitry configured to modify the signal from the MOS gas sensor using a compensation factor, the compensation factor being selected based on the determined dew point.

Another aspect of the present invention provides for a method of manufacturing a MOS gas sensor system, comprising: providing a MOS gas sensor of a particular model, the MOS gas sensor providing a signal indicative of gas concentration of a target gas in an ambient; determining a compensation factor for the MOS gas sensor selected, and responsive to dew point; and providing analog circuitry configured to modify the signal from the MOS gas sensor using the compensation factor.

Yet another aspect of the present invention provides for a fuel cell system comprising a housing having a fuel gas inlet and an exhaust outlet; at least one ion exchange fuel cell membrane located within the housing, and wherein the ion exchange membrane has opposite sides; an anode electrode mounted on one side of the ion exchange fuel cell membrane, and a cathode electrode mounted on the opposite side of the ion exchange fuel cell membrane; and a MOS gas sensor system including a MOS gas sensor which senses the presence of a fuel in the housing, and which provides a signal indicative of the gas concentration of the fuel in the housing; equipment configured to determine the dew point in the housing; and circuitry configured to modify the signal from the MOS gas sensor using a compensation factor which is selected based upon the determined dew point.

Another aspect of the invention provides a method of compensating a signal from a MOS gas sensor, comprising compensating the signal from the given MOS sensor for the effects of dew point by using a first formula w'=((Log (Rcomp/Ro)+2α)/α) where w' is compensated gas concentration in parts per million, where Ro is resistance in ohms for the given MOS gas sensor at 100 PPM when measured at a dew point compensation factor K of unity, where α represents the sensitivity of the given MOS gas sensor, and by using a second formula Rcomp=10^(Log(Rs)+(Log(K)/Ka)α) where Rs is the output of the given sensor, in ohms, indicative of hydrogen gas concentration when influenced by the effects of dew point, where K is a live variable that, when multiplied by the output of the given sensor, compensates for the effects of dew point, and where Ka is a constant having the fixed value of α for which K factors were optimized and which scales the effect of K factor depending on the sensitivity (α) of the given sensor.

Figure 8:
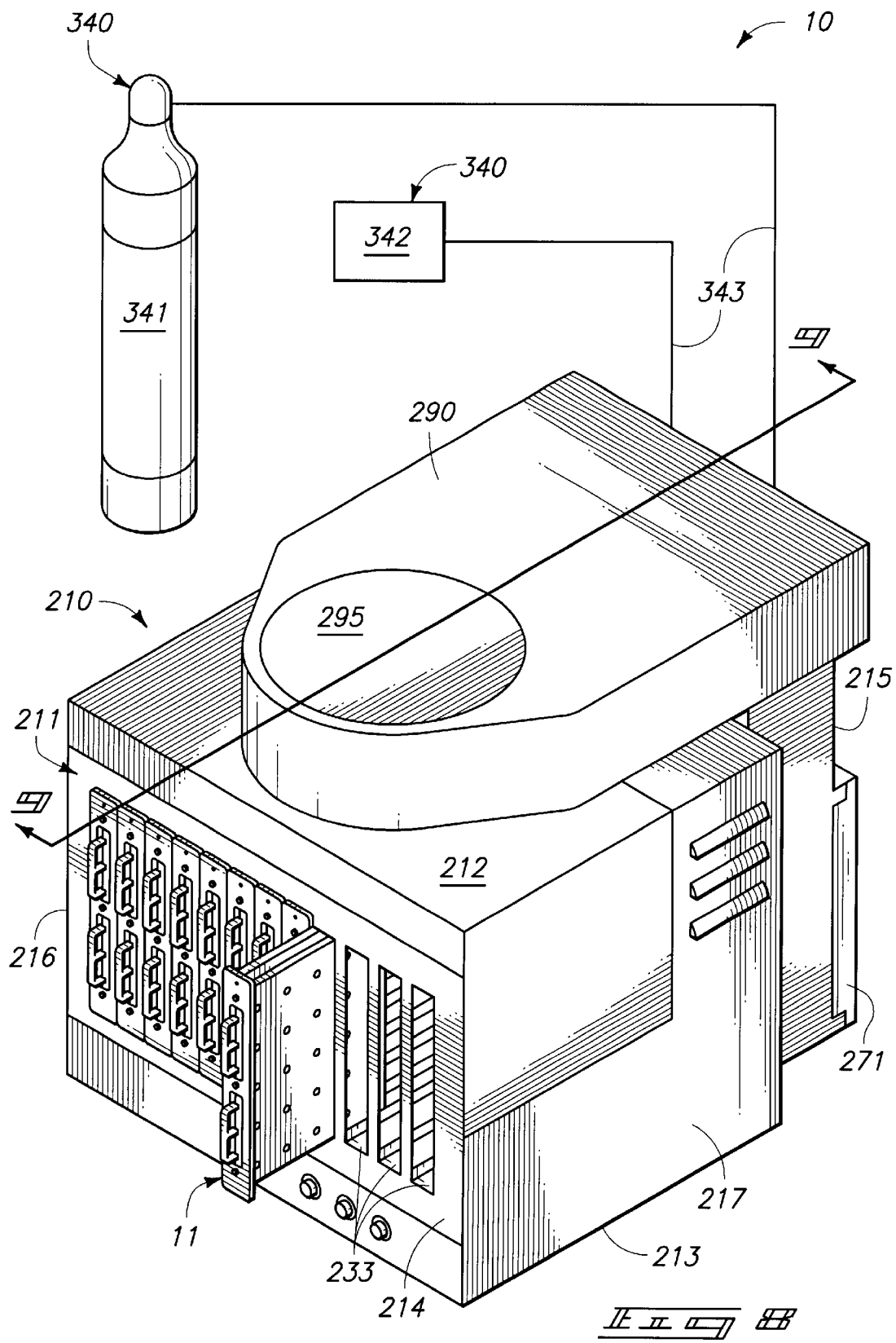
FIG. 8 is a perspective view of an ion exchange membrane fuel cell subrack and associated fuel gas supply.

As best seen in FIG. 8, an ion exchange membrane fuel cell power system 10 is made up of a plurality of fuel cell modules 11, one of which is shown in FIG. 1. The ion exchange membrane fuel cell power system 10 may include a plurality of subsystems or subracks 210. As illustrated each subsystem or subrack 210 includes a plurality of hand manipulable modules 11 (FIG. 1) which respectively have a forward edge 12, an opposite, rearward edge 13, top and bottom surfaces or edges 14 and 15, and opposite sidewalls generally indicated by the numeral 16. Each facet of the module 11 will be discussed in greater detail hereinafter. Yet further those should recognize that the present invention could be employed with conventional stack-like technology wherein the individual subsystem comprises fuel cell stacks arranged in a manner which is consistent with the further teachings of this application.

Figure 2:
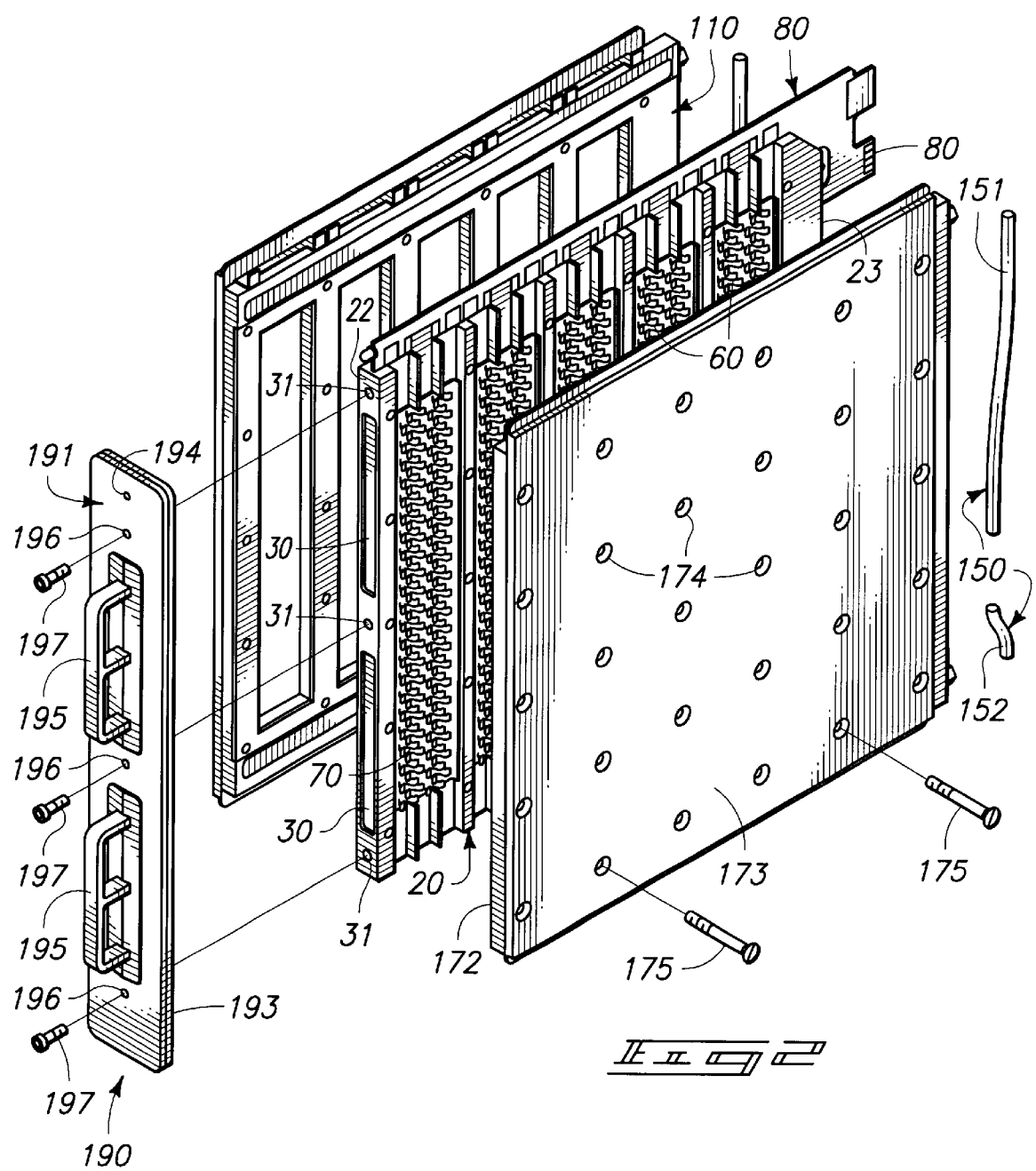
FIG. 2 is a perspective, exploded, side elevation view of an ion exchange membrane fuel cell module as seen in FIG. 1.
Figure 3:
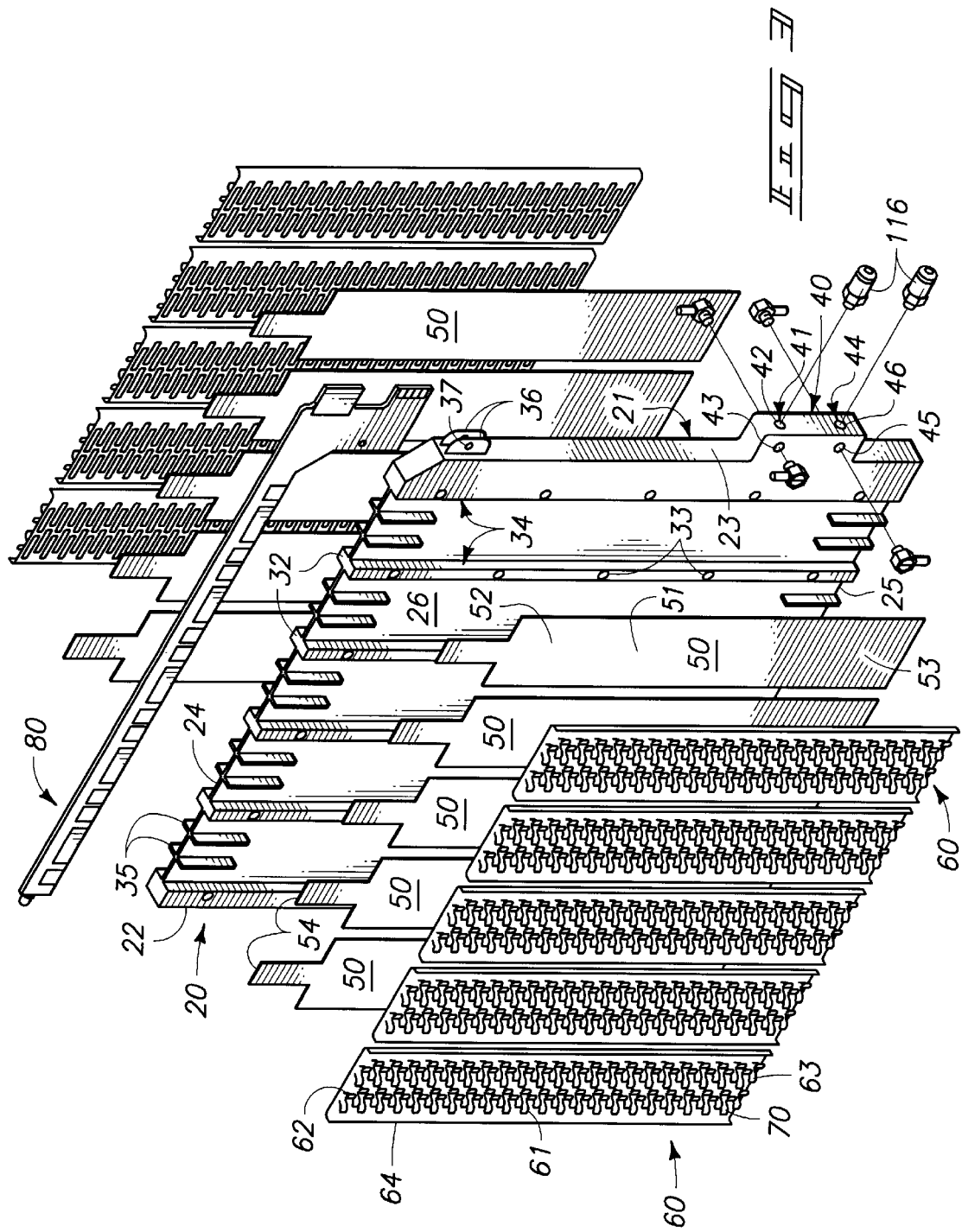
FIG. 3 is a perspective, partial, exploded, side elevation view of an ion exchange membrane fuel cell module as seen in FIG. 1.

As best seen in FIGS. 2 and 3, the fuel cell module 11 includes a nonconductive, dielectric support member generally indicated by the numeral 20. The support member can be fashioned out of various synthetic polymeric substrates.

The support member has (see FIG. 3) a main body 21, which is defined by a forward peripheral edge 22; a rearward peripheral edge 23; a top peripheral edge 24; an opposite, bottom peripheral edge 25; and opposite sidewalls generally indicated by the numeral 26.

As best seen in FIG. 2, a pair of recessed channels 30 are formed in the forward peripheral edge 22. Further, a plurality of fastener receiving passageways or apertures 31 are also formed in the forward peripheral edge 22. Yet further, and as seen in FIG. 3, a plurality of spaced ribs 32 are borne by, or made integral with the respective sidewalls 26 and are disposed in spaced relation, one to the other. Fastener passageways or apertures 33 are formed through each of the ribs. Further, cavities 34 are defined between the respective ribs 32 on each sidewall. The cavities 34 formed on each of the sidewalls are disposed in substantially opposed relation one to the other. This is seen in FIG. 3.

Further, as best seen in FIG. 3, orientation members 35 are disposed between each of the ribs 32 and define a space therebetween. A pair of mounting tabs 36 are provided in spaced relationship, one to the other, on the rearward peripheral edge 23 of the main body 21. A pair of substantially coaxially aligned apertures 37 are individually formed in each of the mounting tabs 36 and are operable to receive a fastener therethrough.

A fuel coupling 40 is made integral with or forms a portion of the rearward peripheral edge 23 of the support member 20. The fuel coupling 40 includes a fuel delivery passageway 41 which is substantially T shaped and which is defined by an intake end 42 and a pair of exhaust ends labeled 43. Additionally, the fuel coupling also includes an exhaust passageway 44 which is also substantially T shaped and which is defined by a pair of intake ends 45, and an exhaust end 46. The operation of the fuel coupling 40 will be discussed in greater detail hereinafter.

As best seen in FIGS. 2 and 3, individual conductor plates generally designated by the numeral 50 are matingly received within the individual cavities 34 which are defined by the support member 20. The conductor plates which are fabricated from an electrically conductive substrate, have a substantially planar main body 51, which has a first end 52, and an opposite, second end 53. The main body 51 further has a conductive tab 54 which extends outwardly relative to the first end 52, and which is oriented between the individual orientation members 35. The conductive tab extends substantially normally outwardly relative to the top peripheral edge 24 of the support member 20. As will be recognized, the main body 51 matingly rests between the individual ribs 32 which define, in part, the respective cavities 34.

As best seen in the exploded view of FIG. 3, a cathode current collector is generally designated by the numeral 60, and rests in ohmic electrical contact with the main body 51 of the individual conductor plates 50. The cathode current collector, which is fabricated from an electrically conductive substrate, has a main body 61 which has opposite first and second ends 62 and 63, respectively. The cathode current collector simultaneously performs the functions of current collection, force application and heat dissipation. Still further, the main body 61 of the current collector 60 is defined by a peripheral edge 64.

Figure 4:
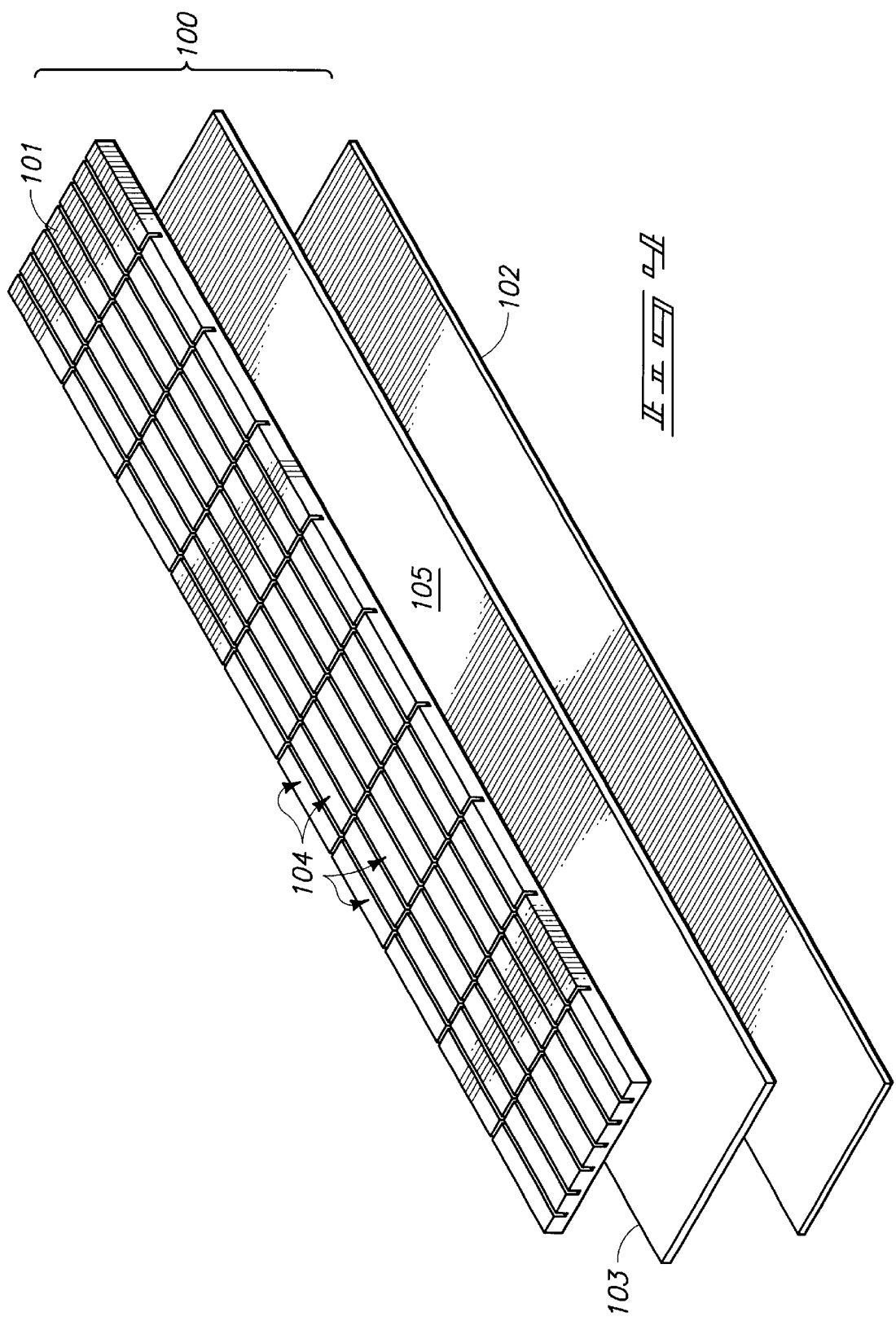
FIG. 4 is a fragmentary, perspective, greatly enlarged, exploded view of a membrane electrode diffusion assembly employed with the ion exchange membrane fuel cell module as seen in FIG. 1.
Figure 7:
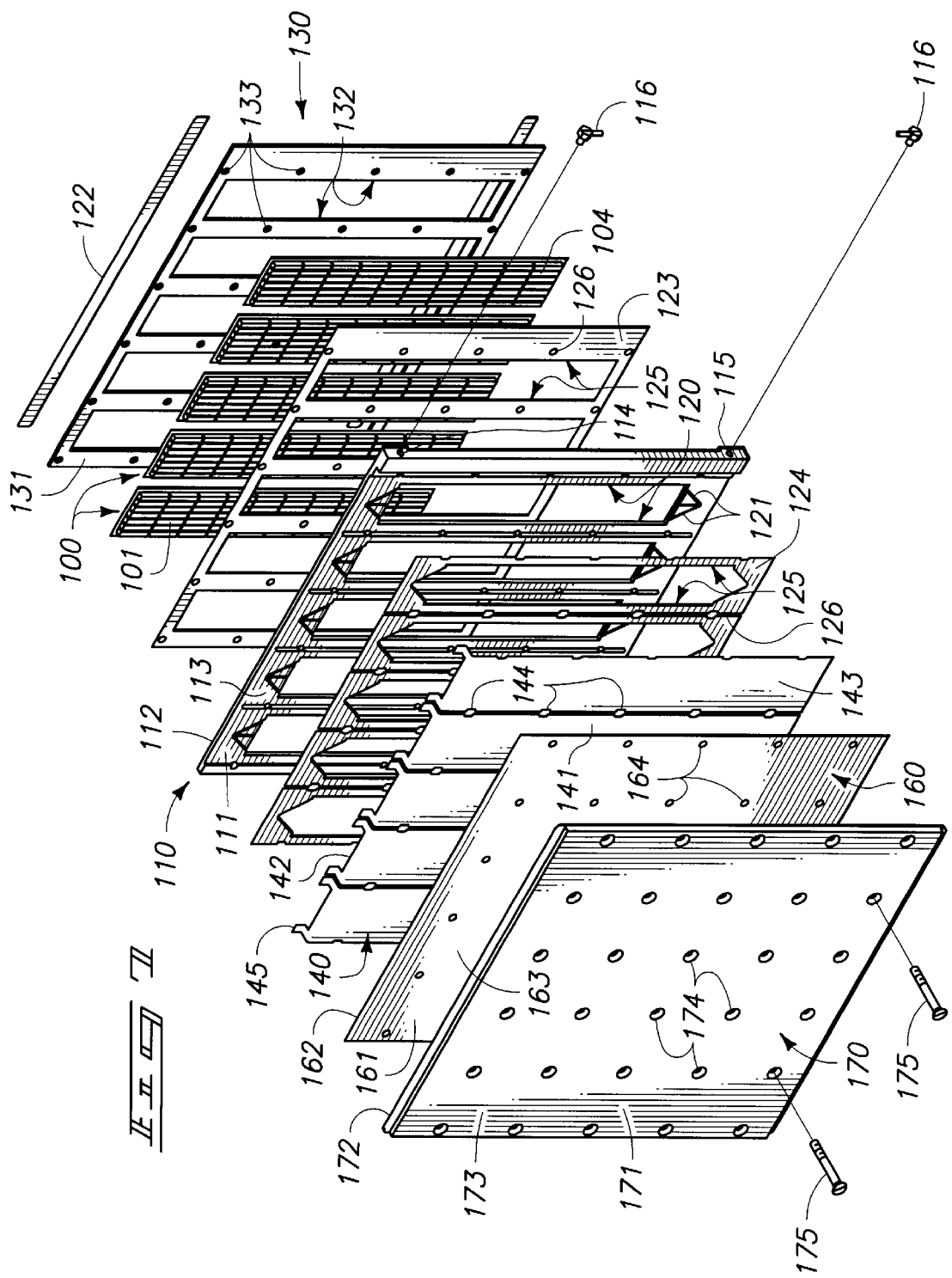
FIG. 7 is a second, perspective, partial, exploded view of a portion of the ion exchange membrane fuel cell module as seen in FIG. 1.
Figure 10:
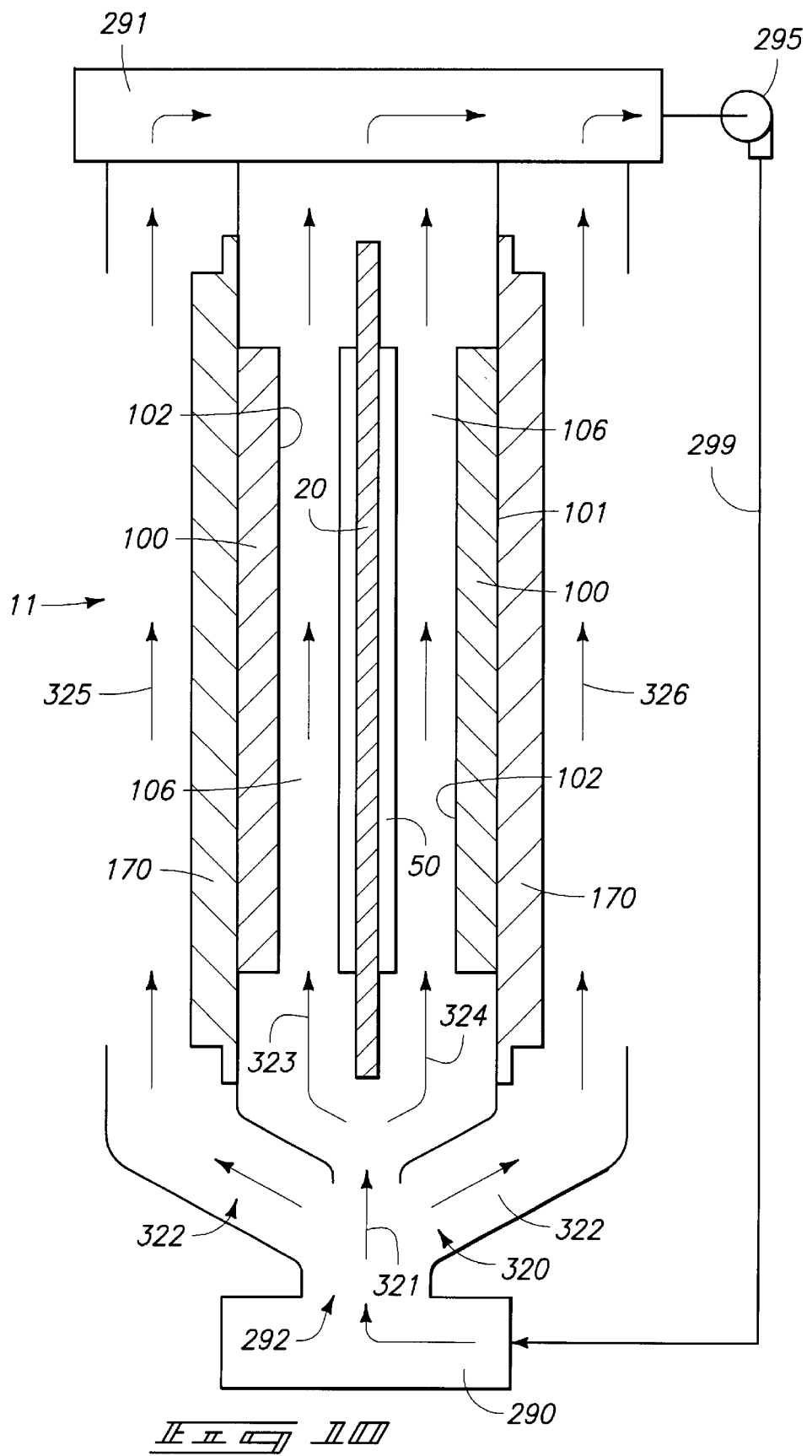
FIG. 10 is a fragmentary, schematic representation of an ion exchange membrane fuel cell module, and associated power system.

As best seen in the exploded view of FIGS. 4 and 7, the ion exchange membrane fuel cell module 11 includes a plurality of membrane electrode diffusion assemblies generally indicated by the numeral 100. Each of the membrane electrode diffusion assemblies have an anode side 101, and an opposite cathode side 102. Still further, each of the membrane electrode diffusion assemblies is defined by a peripheral edge 103, and further has formed in its anode side, a plurality of interlinking channels 104. The membrane electrode diffusion assembly 100, as noted above, is formed of a solid ion conducting membrane 105 which is sealably mounted or received in each of the respective cavities 34. In this arrangement, the cathode side 102 of each membrane electrode diffusion assembly 100 is held in spaced relation relative to the support member 20 by deformable electrically conductive members 70 (FIGS. 2 and 3) of the cathode current collector 60. This spacial arrangement, which is provided by the cathode current collector, facilitates, in part heat dissipation from the fuel cell module 11. As described, above, the membrane electrode diffusion assembly 100; associated cathode current collector 60; and support member 20 in combination, define a cathode air passageway 106 therebetween (FIG. 10). The construction of a suitable membrane electrode diffusion assembly was described in our earlier U.S. Pat. No. 6,030,718. This earlier patent is incorporated by reference herein, and further discussion regarding the construction of the membrane electrode diffusion assembly is not undertaken herein.

As will be appreciated, from a study of FIG. 10, the cathode air passageway 106 is defined or otherwise oriented on each side 26 of the support member 20. Therefore, the fuel cell module 11 has a bifurcated cathode air flow. As will be appreciated, while the earlier described membrane electrode diffusion assembly was directed to a proton exchange membrane, the fuel cell power system 10 is not limited solely to a type having proton exchange membranes, but also may utilize anion exchange membranes.

Figure 5:
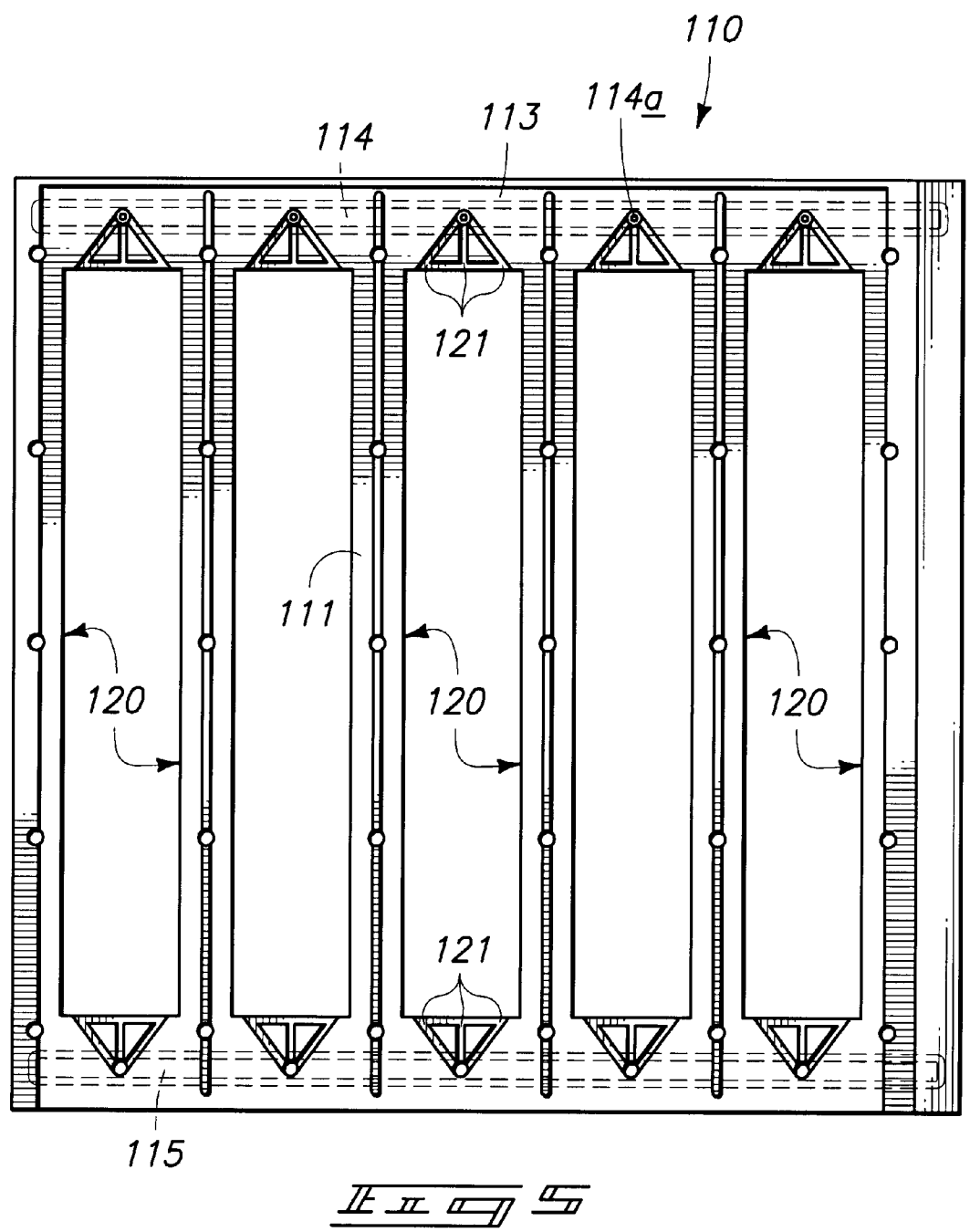
FIG. 5 is a fragmentary, side elevational view of a fuel distribution assembly utilized with the ion exchange membrane fuel cell module as seen in FIG. 1.
Figure 6:
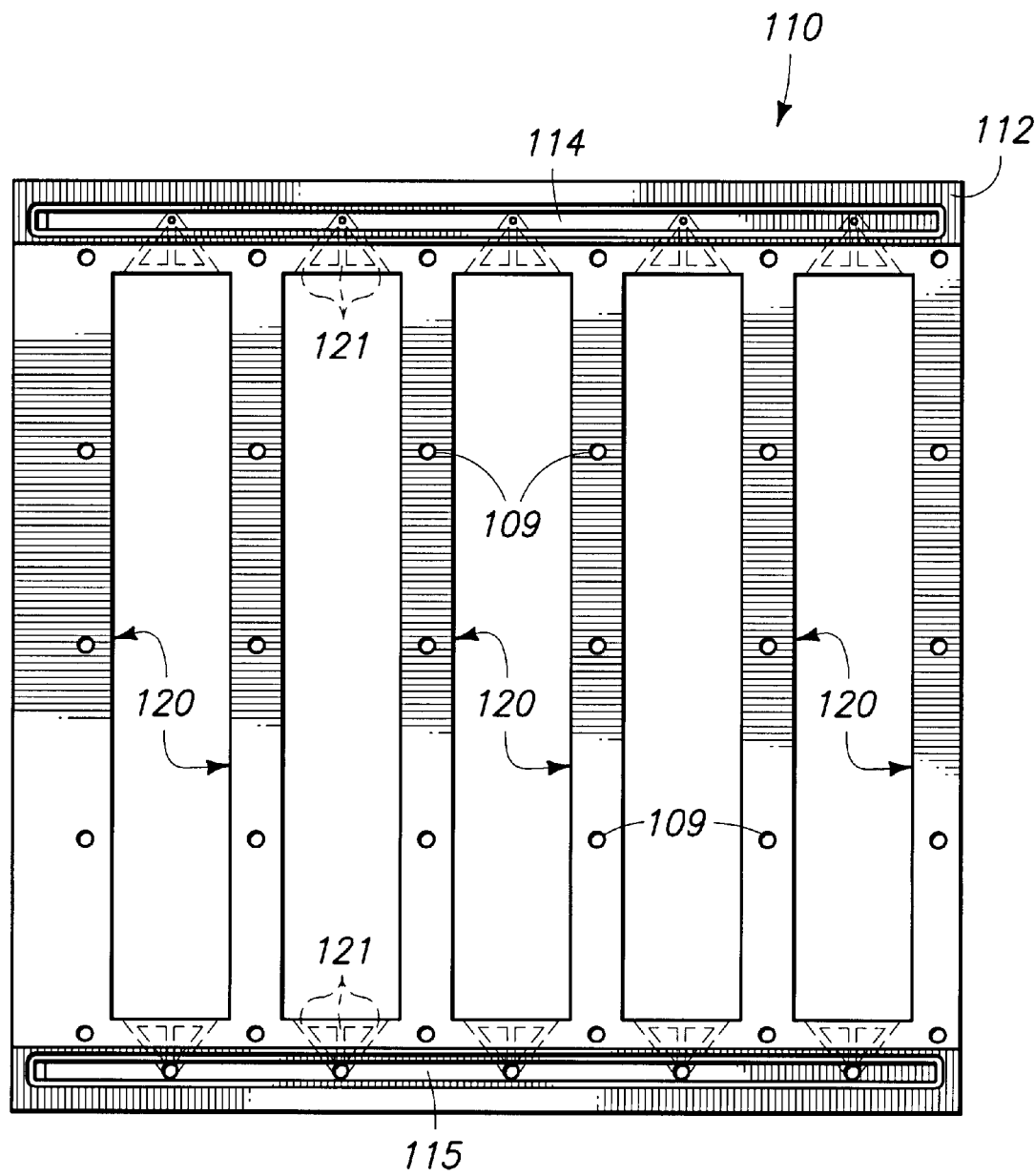
FIG. 6 is a second, fragmentary, side elevational view of the fuel distribution assembly taken from a position opposite to that seen in FIG. 5.

As best seen by reference to FIGS. 5, 6 and 7, a fuel distribution assembly, which is generally indicated by the numeral 110, is coupled in fluid flowing relation relative to the anode side 101 of each of the membrane electrode diffusion assemblies 100. Each fuel distribution assembly 110 is coupled with a source of a fuel 340 (FIG. 8) which may be substantially pure, or which is diluted to various degrees. Such may be achieved if the fuel cell power system was coupled with a fuel processor which would produce a stream of hydrogen from a source of hydrocarbon fuel such as gasoline, natural gas, propane, etc. If the fuel cell power system 10 was fabricated in the nature of a proton exchange membrane fuel cell, the dilute fuel supply would include hydrogen. The concentration of the hydrogen in the dilute fuel would normally be in a range of about 30% to about 80% by volume.

When supplied with this dilute fuel mixture (regardless of the type), the fuel cell modules 11 produce an average current density of at least about 350 mA per square centimeter of surface area of each anode side 101 at a nominal voltage of 0.5 volts. Further, the interlinking channels 104 formed in the surface of the anode side 101 facilitate the distribution of the dilute fuel substantially about the entire surface area of the anode side 101. In this arrangement, if contaminants are introduced by way of the dilute fuel mixture or other blockage occurs, the interlinking channels 104 provide a convenient passage by which the fuel may reach substantially the entire surface area of the anode side 101, even though some portions of the interlinking channels 104 may be blocked or otherwise substantially occluded. As noted above, the dilute fuel 340 may be supplied by a fuel processor 342 (FIG. 8) which receives a hydrocarbon based fuel, and then through a chemical reaction fractionates the hydrocarbon fuel source to liberate a dilute stream of hydrogen which is mixed with other substances. In the alternative, the fuel may be supplied by a pressurized container 341. These alternative arrangements are shown in FIG. 8.

As best seen by reference to the exploded view as shown in FIG. 7 and FIG. 1, the ion exchange membrane fuel cell module of the present invention includes a pair of the fuel distribution assemblies 110 which are individually mounted in fluid flowing relation relative to the anode side 101 of the respective membrane electrode diffusion assemblies 100.

As best seen in FIGS. 5 and 6, each of the fuel distribution assemblies 110 include a main body 111 which has an inside facing surface 112, (FIG. 6) and an outside facing surface 113 (FIG. 5). The main body 111 further defines an intake plenum 114, and an exhaust plenum 115. Further, a fluid coupling 116 (FIG. 1) is mounted in fluid flowing relation relative to the individual intake and exhaust plenums 114 and 115 respectively. A reduced dimension orifice 114a (FIG. 5) is formed in the main body and communicates with the intake plenum 114. This reduced diameter orifice operates to create a pressure differential in the respective apertures or cavities 120 during certain operational conditions to facilitate the clearance of contaminants or other obstructions which may be blocking any of the channels 104 which are formed in the membrane electrode diffusion assembly 100. A plurality of cavities or apertures 120 are formed in the main body 111, and extend between the inside and outside facing surfaces 112 and 113 respectively. The cavities or apertures 120 are disposed in spaced relation, one to the other, and when assembled, the cavities 120 receive the individual membrane electrode diffusion assemblies 100. As best seen in FIG. 5, a plurality of channels or passageways 121 are formed in the main body 111, and couple the individual cavities 120 in fluid flowing relation with the respective intake and exhaust plenums 114 and 115. Additionally, a plurality of fastener apertures 109 are formed in the main body. As further seen in FIG. 7, a sealing member 122 lies in covering relation relative to the individual channels 121.

As best seen in FIG. 1, a plurality of conduits 150 couple in fluid flowing relation the fuel coupling 40 with the fuel distribution assembly 110. Two of the conduits designated as 151 allow a dilute fuel mixture to be delivered by way of the intake plenum 114 to the individual membrane electrode diffusion assemblies 100. Thereafter, any remaining fuel, and associated by-products of the chemical reaction are received back into the exhaust plenum 115 and then flow by way of conduits 152 to the fuel coupling 40 and then to the exhaust passageway 44.

First and second pressure sensitive adhesive seals 123 and 124 (FIG. 7), respectively are provided, and are disposed in juxtaposed relation relative to the opposite inside and outside facing surfaces 112 and 113 respectively. Each of the seals 123 and 124 have apertures 125 formed therein which are substantially coaxially oriented relative to the respective cavities 120. As will be recognized, the cavities 120 which are formed in the main body 111 of the fuel distribution assembly 110, matingly cooperate and are substantially coaxially aligned with the individual cavities 34 which are formed in the nonconductive support plate 20. As will be recognized and following the assembly of same, the respective membrane electrode diffusion assemblies 100 are individually received in mating relation in each of the cavities 120 and 34 which are defined by both the fuel distribution assembly 110, and the support member 20. Further, a plurality of fastener apertures 126 are formed in the individual seals 123, and 124, and are operable to receive fasteners which will be discussed in greater detail hereinafter.

Lying in immediate juxtaposed relation relative to the second pressure sensitive adhesive seal 124 is an anode current collector which is generally designated by the numeral 140. Additionally, and as seen in FIG. 7, a substantially rigid sealing plate 130 is provided and which is juxtaposed relative to the cathode side 102 of the membrane diffusion assembly 100. The sealing plate 130 has a main body 131 which defines a plurality of apertures 132 which matingly receive, in part, the respective membrane electrode diffusion assemblies 100. Still further, the main body has a plurality of fastener apertures 133 formed therein and which when assembled, are substantially coaxially aligned with the aforementioned fastener apertures formed in the earlier described portions of the fuel cell module 11.

Each anode current collector 140 lies in ohmic electrical contact against the anode side 101 of each of the membrane electrode diffusion assemblies 100 and further is oriented in heat receiving relation relative thereto. The anode current collector 140 has an electrically conductive main body 141 which has an inside facing surface 142 which lies against the anode side 101 of the membrane electrode diffusion assembly 100, and an opposite outside facing surface 143. Still further, a plurality of fastener apertures 144 are formed in the main body 131 and are operable to be substantially coaxially aligned relative to the other fastener apertures 126 formed in the various seals 123, 124, and in the fuel distribution assembly 110.

As seen in FIG. 7, an electrically insulative member or gasket 160 is mounted or oriented in juxtaposed relation relative to the outside facing surface 143 of the anode current collector 140. This insulative member has a main body 161 which has an inside facing surface 162 which rests in contact with the outside facing surface 143 of the anode current collector, and further has an outside facing surface 163. Further, a plurality of fastener apertures 164 are operable to be coaxially aligned with the previously described fastener apertures formed in the remaining parts of the ion exchange membrane fuel cell power system 10.

As best seen in FIG. 7, an anode heat sink 170 is oriented in juxtaposed relation relative to the insulative member 160, and further, is mounted in heat receiving relation relative to the anode sides 101 of each of the membrane electrode diffusion assemblies 100 to conduct heat energy generated by the ion exchange membrane module 11 away from the membrane electrode diffusion assembly 100. In this arrangement, the fuel distribution assembly 110 is located substantially between the anode side 101 of the membrane electrode diffusion assembly 100, and the anode current collector 140. The anode heat sink 170 has a main body 171 which has an inside facing surface 172, which lies in juxtaposed relation relative to the insulative member 160, and an opposite outside facing surface 173. Similarly, and as discussed above, numerous fastener apertures 174 are formed therein, and which are substantially coaxially aligned with the remaining fastener apertures which are formed in the earlier disclosed portions of the ion exchange membrane fuel cell module 11. Fasteners 175 are provided and are received in these coaxially aligned fastener apertures such that the module is held firmly together. These fasteners 175 along with the respective current collectors 60 create sufficient pressure to allow the individual current collectors 60 and 140 to make effective ohmic electrical contact with the anode and cathode sides 101 and 102, respectively, of the membrane electrode diffusion assembly 100. As will be recognized from the discussion above, the anode current collector 140 is substantially electrically isolated from the anode heat sink 170. Additionally, the anode heat sink has sufficient thermal conductivity such that it substantially inhibits the formation of a temperature gradient across the membrane electrode diffusion assembly 100 during operation of the ion exchange membrane fuel cell power system 10.

A handle assembly is generally indicated by the numeral 190 and is best seen in FIG. 2. As shown therein, the handle assembly 190 has a back plate generally indicated by the numeral 191, and which is defined by a front surface 192, and an opposite rear surface 193. Formed through the front and rear surfaces is an aperture 194 which matingly receives the member 84 which is mounted on the main body 81 of the current conductor assembly 80. Still further, pair of handles 195 are fastened on the front surface 192, and additionally, a plurality of fastening apertures 196 are formed through the front and rear surfaces 192 and 193 and are operable to receive fasteners 197 which threadably engage the fastener apertures 31, which are formed in the forward edge 23 of the support member 20. The handles permit the module 11 to be easily manipulated by hand, and removed without the use of any tools, when utilized with a subrack or sub-system which will be discussed in greater detail hereinafter.

Figure 9:
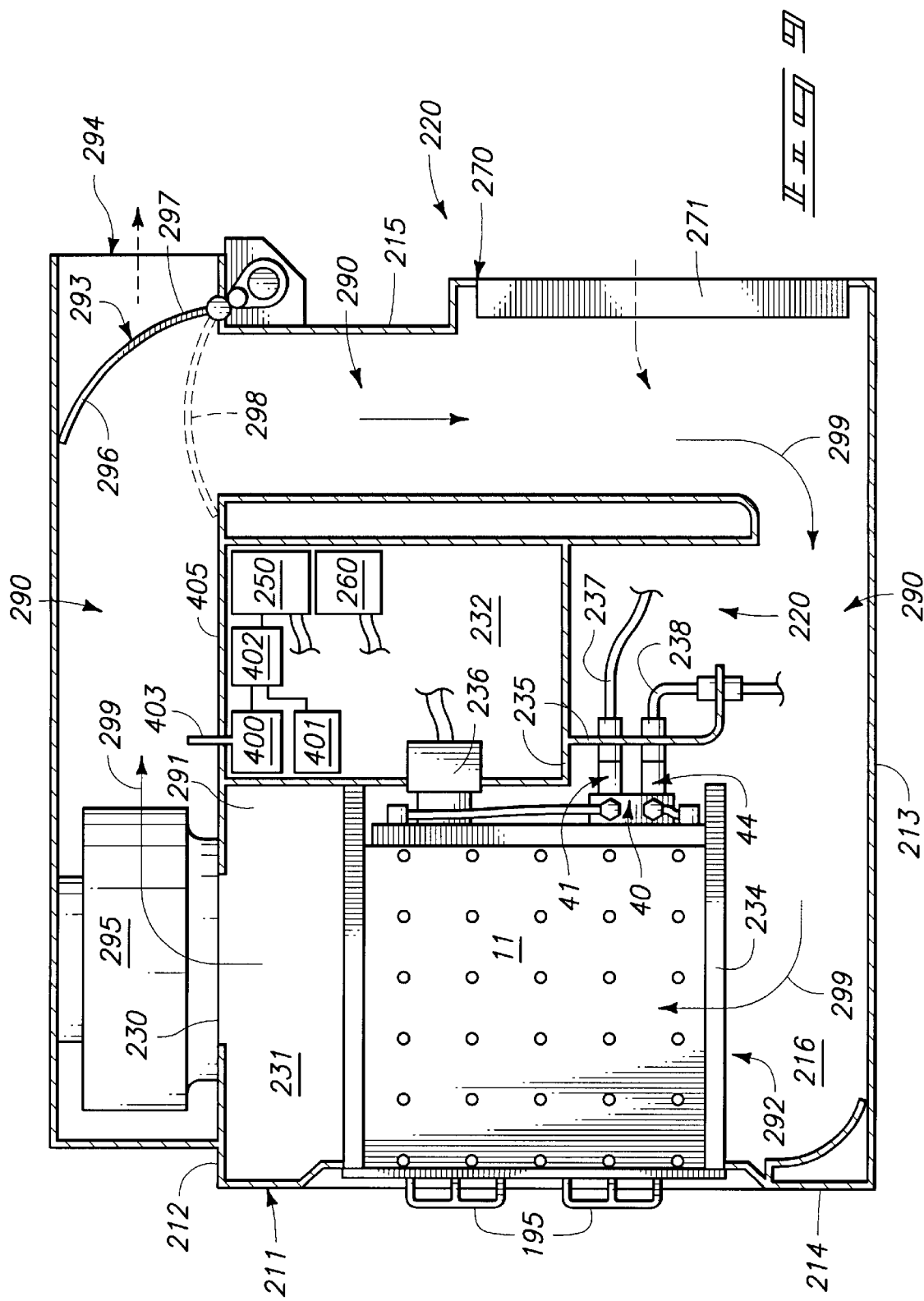
FIG. 9 is a fragmentary, transverse, vertical sectional view taken from a position along line 9—9 of FIG. 8.

The ion exchange membrane fuel cell module 11 is employed in combination with a plurality of subracks or sub-systems 210, one of which is shown in FIGS. 8 and 9 and which is generally indicated by the numeral 210. Each subrack 210 releasably supports a plurality of ion exchange membrane fuel cell modules 11 in an operable arrangement. Each subrack 210 includes a principal enclosure 211. The principal enclosure is defined by a top surface 212; bottom surface 213; front sidewall 214; rear sidewall 215; left sidewall 216, and right sidewall 217. The respective sidewalls 212 through 217 define an internal cavity 220 (FIG. 9). In this arrangement, the principal enclosure will receive multiple fuel cell modules 11, each enclosing a membrane electrode diffusion assembly 100.

As seen in FIG. 8, the ion exchange membrane fuel cell power system is configured in a manner where at least one of the fuel cell modules 11 can be easily removed from at least one of the subracks 210 by hand, while the remaining modules continue to operate. As noted above this removal is normally accomplished without the use of any tools, however it may be necessary in some commercial or industrial applications where vibration, and other outside physical forces may be imparted to the system, to use threaded fasteners and the like to releasably secure the individual modules to the subrack 210 to prevent the unintentional displacement or dislocation of the respective modules from the subrack 210. If utilized, the hand tools which will be employed will be simple hand tools, and the removal will be accomplished in minutes, as opposed the prior art stack arrangements where replacement of a damaged membrane electrode assembly (MEA) may take hours to accomplish. It should be understood that the terms "subrack" and "sub-system" as used in the following claims do not necessarily imply that a rack or shelf is required, only that the sub-system, or a portion thereof, is operable independently whether or not other sub-system, or a portion thereof, of the fuel cell power system 10 are functioning.

As best seen by reference to FIG. 9, an aperture 230 is formed in the top surface 12 of the subrack 210, and further, the cavity 220 is comprised of a first or fuel cell module cavity 231, and a second cavity or electrical control bay 232. As best seen by reference to FIG. 8, a plurality of individual module apertures 233 are formed in the front surface 214 of the principal housing 211, and are operable to individually receive the respective fuel cell modules 11, and position them in predetermined spaced relation, one to the other.

The fuel cell module cavity 231 is further defined by a supporting member or shelf 234 (FIG. 9) which orients the individual fuel cell modules 11 in a predetermined substantially upright orientation within the cavity 231. Additionally, the fuel cell module cavity 231 is defined by a rear wall 235 which supports a DC bus 236 in an orientation which will allow it to releasably, matingly, electrically couple with the current conductor assembly 80 (FIG. 2) which is borne by the fuel cell module 11. Yet further, and as seen in the cross sectional view of FIG. 9, the rear wall 235 further supports a fuel supply line 237 and a byproduct removal line 238. These are operable to be releasably coupled in fluid flowing relation with respect to the fuel delivery passageway 41 and the exhaust passageway 44 of the fuel coupling 40.

As best seen in FIG. 9, the second cavity or electrical control bay 232 encloses a digital or analog controller 250 which is electrically coupled with the respective ion exchange membrane fuel cell modules 11, and a power conditioning assembly 260 which is electrically coupled with the DC bus 236, and the controller 250, and which is operable to receive the electrical power produced by the ion exchange membrane fuel cell modules 11. The operation of the controller 250 and power conditioning assembly 260 and related control circuitry is discussed in prior U.S. application Ser. Nos. 09/108,667 and 09/322,666, which are incorporated by reference herein.

As further seen in FIG. 9, an aperture 270 is formed in the rear wall 215 of the principal enclosure 211, and is operable to receive an air filter 271 which is operable to remove particulate matter from an outside ambient air stream passing therethrough and into the principal enclosure 211.

As best seen by the cross sectional view in FIG. 9, the subrack 210 includes an air distribution plenum 290 which is coupled in fluid flowing relation relative to each of the ion exchange membrane fuel cell modules 11. The air distribution plenum 290 has a first or intake end 291 which receives both air which has previously come into contact with each of the ion exchange fuel cell modules 11, and air which comes from outside of the respective ion exchange membrane fuel cell modules. Further, the air distribution plenum has a second or exhaust end 292 which delivers an air stream to each of the ion exchange fuel cell modules 11. Disposed intermediate the first or intake end 291, and the second or exhaust end 292 is an air mixing valve 293 which is coupled to the air distribution plenum 290, and which meters the amount of air which is passed through the respective ion exchange membrane fuel cell modules 11 and is recirculated back to the ion exchange fuel cell membrane modules and by way of the air filter 271. As illustrated, the mixing valve 293 selectively occludes an aperture 294 which is formed in the rear wall 215 of the subrack 210.

An air movement assembly such as a fan 295 is provided and is mounted along the air distribution plenum 290. As shown in FIG. 9, the air movement assembly 295 is positioned near the intake end 291, and is substantially coaxially aligned with the aperture 230 which is formed in the top surface 212 of the subrack 210. The air mixing valve and the fan assembly 293 and 295 respectively are electrically coupled with the controller 250 and are controlled thereby. The air mixing valve 293 comprises a pivotally movable valve member 296 which can be moved from a first occluding position 297 relative to the aperture 294, and a second, substantially non-occluding position 298 as shown in phantom lines.

As will be recognized, when the valve member 296 is in the second non-occluding position, air received in the intake end 291 and which has previously passed through the individual fuel cell modules will pass out of the principal enclosure 211 and then be exhausted to the ambient environment. On the other hand, when the valve member 296 is in the occluding position 297 air from the intake end 291 which has passed through the fuel cell module 11 will return to the exhaust end and then pass through the modules 11 and return again to the intake end. As will be recognized, by controlling the relative position of the valve member 296, temperature as well as relative humidity of air stream 299 can be easily controlled. Still further, in the occluding position 297, air from the ambient will continue to enter the air distribution plenum by way of the air filter 270.

More specifically, the air stream 299 which is supplied to the fuel cell modules is provided in an amount of at least about 5 to about 1000 times the volume required to support a fuel cell chemical relation which produces water vapor as a byproduct. The present air plenum arrangement provides a convenient way by which the air stream delivered to the cathode side 102 can be humidified by the water vapor generated as a byproduct of the chemical reaction taking place on the cathode. Additionally, during cold operating conditions, this same air, which has now been heated by each of the fuel cell modules 11, will contribute to bringing the entire fuel cell up to normal operating temperatures. Further, the air mixing valve 293 limits the amount of air which has previously passed through the modules 11 and which is added to the air distribution plenum 290. This resulting recirculated air stream and fresh ambient air forms an air stream having substantially optimal operating characteristics which maximizes the current densities and outputs of the respective membrane electrode diffusion assemblies enclosed within each of the fuel cell modules 11.

Referring now to FIG. 10, what is shown is a greatly simplified, exaggerated, partial, and cross-sectional view of an ion exchange membrane fuel cell module 11 positioned in an operational relationship relative to the air distribution plenum 290. This particular sectional view, which does not include many of the subassemblies previously discussed, is provided to illustrate the principals that will be set forth below. As seen in FIGS. 9 and 10, and as discussed above, the subrack 210 includes an air distribution plenum 290 which provides a stream of air 299 to each of the ion exchange fuel cell modules 11 which are received in an operational position on the shelf or supporting member 234. The air stream 299 exits from the exhaust end 292 and then becomes a bifurcated air flow which is generally indicated by the numeral 320. The bifurcated air flow 322 comprises a first cathode air stream 321, which is received in the respective ion exchange membrane fuel cell modules 11; and a second anode heat sink air stream which is generally indicated by the numeral 322. As will be recognized by a study of FIG. 10, the first cathode air stream 321 enters the ion exchange membrane fuel cell module 11, and is further bifurcated into a first component 323 which moves along one of the cathode air passageways 106 which is defined on one side of the support member 20. Further, the first cathode air stream 321 has a second component 324 which passes along the cathode air passageway 106 on the opposite side of the support member 20. As will be appreciated, the bifurcated cathode air stream 321 provides the necessary oxidant (oxygen in the ambient air stream) to the cathode side 102 of the membrane electrode diffusion assembly 100. Yet further, the cathode air flow operates to remove less than a preponderance of the heat energy generated by the membrane electrode diffusion assembly 100 while it is in operation. As will be recognized the cathode air flow is facilitated by the respective cathode current collectors 60 which create in part, the cathode air passageway 106.

The anode heat sink air stream 322 is further bifurcated into a first component 325 and a second component 326, both of which individually move along the opposite sides 16 of the ion exchange membrane fuel cell module 11, and over each of the anode heat sinks 170. As the anode heat sink air stream components 325 and 326 move over the opposite anode heat sinks 170, the anode heat sink air stream operates to remove a preponderance of the heat energy generated by the ion exchange membrane fuel cell module 11 during operation. Therefore, it will be recognized that the present invention provides an ion exchange fuel cell module 11 which has a bifurcated air flow 320 which regulates the operational temperature of the ion exchange membrane fuel cell module by removing the heat energy generated therefrom.

Referring now to FIG. 8, and as earlier discussed, the individual ion exchange membrane fuel cell modules 11 and the subrack 210 comprise in combination a fuel cell power system which is coupled in fluid flowing relation relative to a source of a substantially pure or dilute fuel generally indicated by the numeral 340. The fuel gas supply may comprise a source of bottled and compressed fuel gas generally indicated by the numeral 341, or a fuel stream which is provided by a chemical reactor, or fuel processor 342 which produces the fuel stream for use by the individual ion exchange fuel cell modules 11. A conduit 343 couples either fuel gas supply 340 with the respective ion exchange fuel cell modules 11 and the associated subrack 210. When a chemical fuel processor 342 is provided, the fuel processor would receive a suitable hydrocarbon fuel stream such as natural gas, propane, butane, and other fuel gases and would thereafter, through a chemical reaction release a fuel stream which would then be delivered by way of the conduits 343.

The present fuel cell power system 10 may also include a fuel gas recovery and recycling system (not shown) which would recover or recapture unreacted fuel gas which has previously passed through the individual ion exchange fuel cell modules 11. This system, in summary, would separate the unreacted fuel gas and would return the unreacted fuel gas back to the individual ion exchange fuel cell modules for further use. This recovery system would be coupled with the byproduct removal line 238.

Although a certain number of subracks 210 are shown in the drawings, and a certain number of fuel cell modules 11 are shown per subrack 210, it will be readily apparent that any desired number of subracks and modules 11, or a portion thereof, could be employed in alternative embodiments.

The fuel cell power system 10 (FIG. 9) includes one or more gas sensors 400 in one or more locations and which are used, for example, to detect the presence of fuel (e.g., hydrogen gas). The presence of hydrogen gas in certain areas of the fuel cell power system 10 of the subracks 210 may indicate a fuel leak. Such fuel leaks can be potentially hazardous under certain operating conditions. One such sensor 400 is shown in FIG. 9. The sensor 400 has a sampling port 403, including a sensor element, and a baffle protecting the sensor element; e.g., from high velocity airflow. The sampling port 403 is the part of the sensor primarily exposed to the target gas. In one embodiment, the baffle comprises a sintered bronze disk. Other alternatives could be employed. For example, the baffle could just as easily be a piece of chemist's filter paper. Further, if the sampling port 403 is located in an area that does not have ventilation or high airflow, the baffle is not necessary and can be omitted altogether.

The sensor 400 includes a heater for heating the sensor element to a predetermined operating temperature. The heater can be, for example, a wire that is spirally wound relative to the sensor element. Such heaters provide heat in a predefined temperature range to assure proper operation of the accompanying sensor. Other configurations are, of course, possible for the sensor 400. In operation, an electrical current is applied to the heater associated with the sensor 400, at a predetermined power level, to maintain the element at a specified operational temperature. For example, with one commercially available sensor, approximately 600 mW of power maintains the sensor at a temperature of 500° C.

The fuel cell power system 10 further includes circuitry 402 which is electrically-coupled to the sensor 400. The circuitry 402 controls operation of the sensor 400 (e.g. generation of heat by the heater included in the sensor 400) and further is coupled to the controller 250. In one embodiment, the circuitry 402 is a printed circuit card associated with the sensor 400 and which is provided by the manufacturer thereof.

In one embodiment, for example (see FIG. 9), the gas sensor 400 is positioned such that it may sense hydrogen gas in the plenum 290. In this embodiment, the gas sensor 400 is primarily housed in the cavity or electrical control bay 232. The circuitry 402 associated with the card (discussed above) is also located in the electrical control bay 232 and is mounted, for example, on ¼-inch-long standoffs which are affixed to the top of the control bay 232. As seen in FIG. 9, the sampling port disk 403 protrudes through the bulkhead 405 separating the chamber 232 and the plenum 290 in order to position the sampling port 403 inside plenum 290.

Other locations for the sensor 400 are, of course, possible. The location is, in the illustrated embodiment, selected such that the sampling port 403 is positioned downstream of the fan 295. This location insures that leaking hydrogen is homogenized into the air, but is detected before encountering any mixing vanes 293, or where fresh air is introduced 271. Further, the location, in the illustrated embodiment, is selected such that the circuitry 402 and the electrical connector between the circuitry 402 and the sensor 400 are located within the control bay 232 so that this connector does not have to pierce the bulkhead 405. This also allows the electronics of the circuitry 402 to be located in an area that is cooled via fan-forced air.

Alternatively, the sensor 400 may be located in the plenum 290 and the electrical connector between the circuitry 402 and the sensor 400 must then pierce the bulkhead 405. This is less desirable because the fuel cell system 10 circulates air at about 55 degrees C. and this higher temperature lessens the life of power-producing electronic components on the circuitry 402. Further, a seal is required where the cable pierces the bulkhead 405.

The fuel cell power system 10 further includes dew point determining equipment 401. In one embodiment of the invention, the dew point determining equipment comprises chilled-mirror equipment, configured to provide a signal representative of the dew point. Chilled-mirror dew point determining equipment is described, in greater detail, in the following U.S. patents which are incorporated herein by reference: U.S. Pat. Nos. 5,739,416 to Hoenk; 5,507,175 to Cooper; and 6,155,098 to Shapiro et al. In an alternative embodiment, the dew point determining equipment comprises a temperature sensor and a relative humidity sensor.

The fuel cell power system 10 further includes conditioning circuitry 402 which is electrically coupled to the sensor 400 and to the dew point determining equipment 401, for reasons that will be described in greater detail below. In this regard, the conditioning circuitry 402 conditions the output signal of the sensor 400 and provides the conditioned signal to the controller 250.

While other sensors could be employed, in the illustrated embodiment, the sensor 400 is a metal oxide semiconductor (MOS) hydrogen sensor, model TGS 821, and which is commercially available from Figaro Engineering (Figaro). Figaro's sensors are described in the following U.S. patents, which are incorporated herein by reference: U.S. Pat Nos. 5,006,828 to Yutaka et al.; 4,958,513 to Yasunga et al.; 4,938,928 to Koda et al.; 4,827,154 to Naoyuki et al.; 4,816,800 to Onaga et al.; 4,731,226 to Takahata et al.; 4,718,991 to Yamazoe et al.; 4,701,739 to Sasaki; 4,658,632 to Sasaki; 4,575,441 to Murakami et al.; 4,459,577 to Murakami et al.; and 4,117,082 to Matsuyama.

Figure 11:
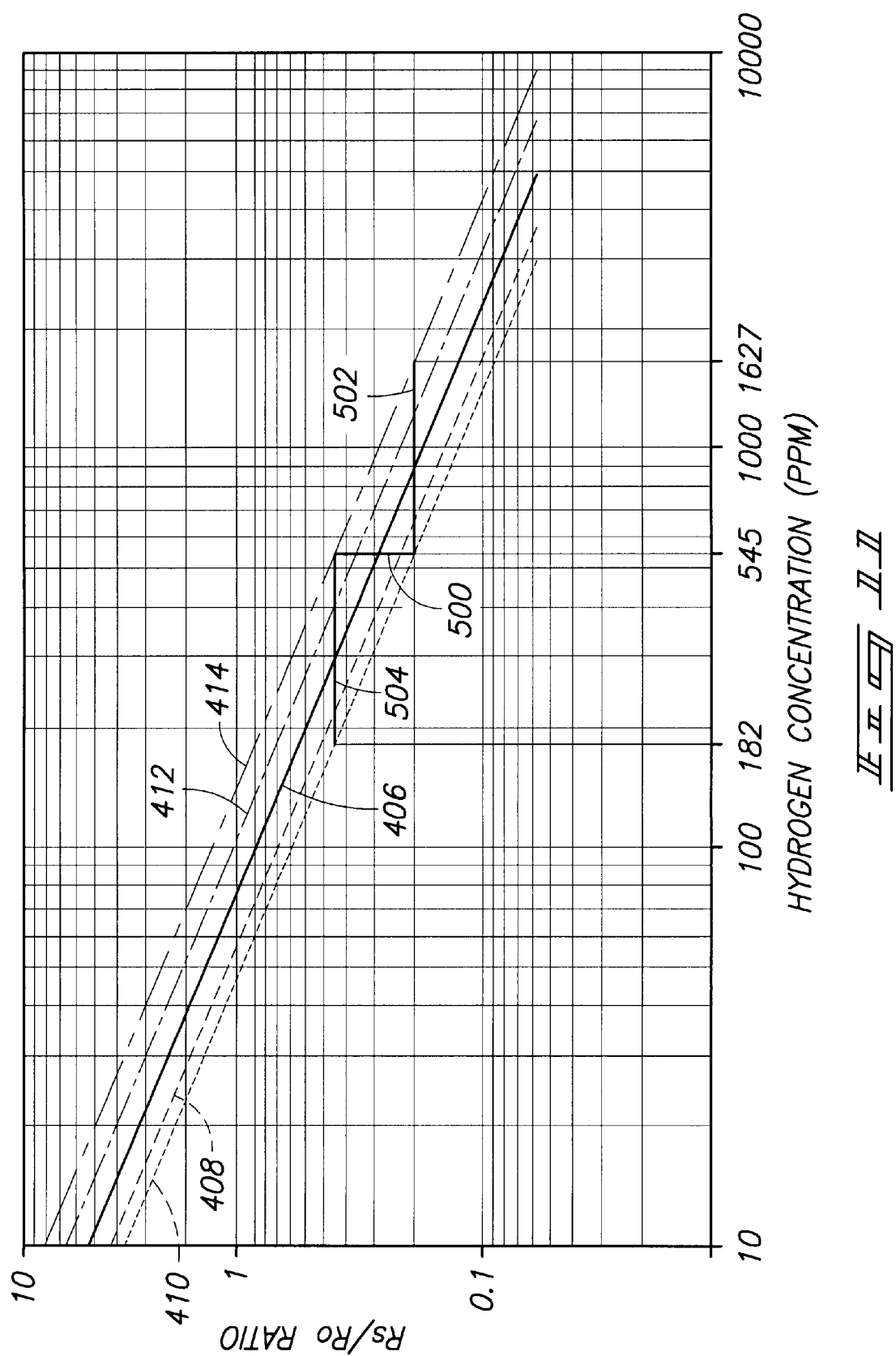
FIG. 11 is a graph illustrating the average ratiometric response of a typical MOS gas sensor to the concentration of a gas used as a fuel in the fuel cell system as illustrated.

FIG. 11 illustrates temperature/humidity dependency. More particularly, FIG. 11 shows the average ratiometric response of one sensor model, the Figaro TGS821, to hydrogen and shows environmental offsets. The relationship between hydrogen concentration versus relative resistance, at an environmental dependency Rs/Ro of unity (where the effects due to temperature and relative humidity are null), can be described by a formula of the form y=mx+b and is given by the function $y=10^{(\alpha Log(w)-2\alpha)}$. Here, "y" is the Rs/Ro ratio and is the sensor's sensitivity ratio normalized to unity at a gas concentration of 100 PPM. The term "w" is the hydrogen gas concentration in PPM. The term "$\alpha$" (alpha) describes the sensor's sensitivity slope (how steep it is). Whereas $\alpha$ for one particular sensor (Figaro TGS821) averages −0.725, manufacturing tolerances are such that a ranges from −0.6 to −1.2. The actual sensor resistance for any given hydrogen concentration at an environmental dependency Rs/Ro of unity, is given by the formula $R=10^{(3.5\pm0.5)y}$. The term "R" is sensor resistance ($\Omega$) and the term "y" is the sensor's sensitivity Rs/Ro ratio. This means that at an environmental dependency Rs/Ro ratio of unity, the average sensor of this model has about 3.2 k$\Omega$ of resistance at 100 PPM, but ranges from 1.0 k$\Omega$ to 10 k$\Omega$. As can be seen, the sensitivity of the sensor defined by the relationship between gas concentration changes and the sensor resistance changes is based on a logarithmic function. The x-axis is gas concentration and the y-axis is indicated as a sensor resistance ratio Rs/Ro where Rs is sensor resistance. In the graph of FIG. 11, the four slopes 408, 410, 412, 414 adjacent to the main (bold) one 406 denote the extent to which temperature and relative humidity—environmental dependencies—can affect the sensor's signal output in fuel cell applications. Slope 406 is an environmental dependency Rs/Ro of unity, slope 408 is an environmental dependency Rs/Ro of 0.8, slope 410 is an environmental dependency Rs/Ro of 0.6835, slope 412 is an environmental dependency Rs/Ro of 1.25, and slope 414 is an environmental dependency Rs/Ro of 1.5109.

Note the error bar 500 on FIG. 11. Without circuitry to compensate for the environmental effects to which fuel cells are subjected, or knowledge of the environmental circumstances, a reported reading of 545 PPM could reside anywhere on the line segment 502 projecting to the right from the bottom of the error bar 500 (at an Rs/Ro ratio of 0.200) and the true concentration could be as great as 1627 PPM. Just as easily, a reported reading of 545 PPM could reside anywhere on the line segment 504 projecting to the left from the top of the error bar (at an Rs/Ro ratio of 0.442) and the true concentration could be as little as 182 PPM. This is an 8.9:1 range of uncertainty and is the source of much frustration with uncompensated MOS gas sensors.

It may also be advantageous to have circuitry associated with a sensor, such as circuitry 402 in the present embodiment, be of an all-analog design (i.e., a design with no microprocessor at the heart of the device continually running firmware or software) in certain embodiments. It should be appreciated that in certain safety-critical applications, it can be very challenging to design both fail-safe microprocessor-based hardware and fail-safe firmware. Yet further, It can be even more challenging—and costly—to prove to nationally recognized testing laboratories that the system is fail-safe under all operating circumstances.

Figure 12:
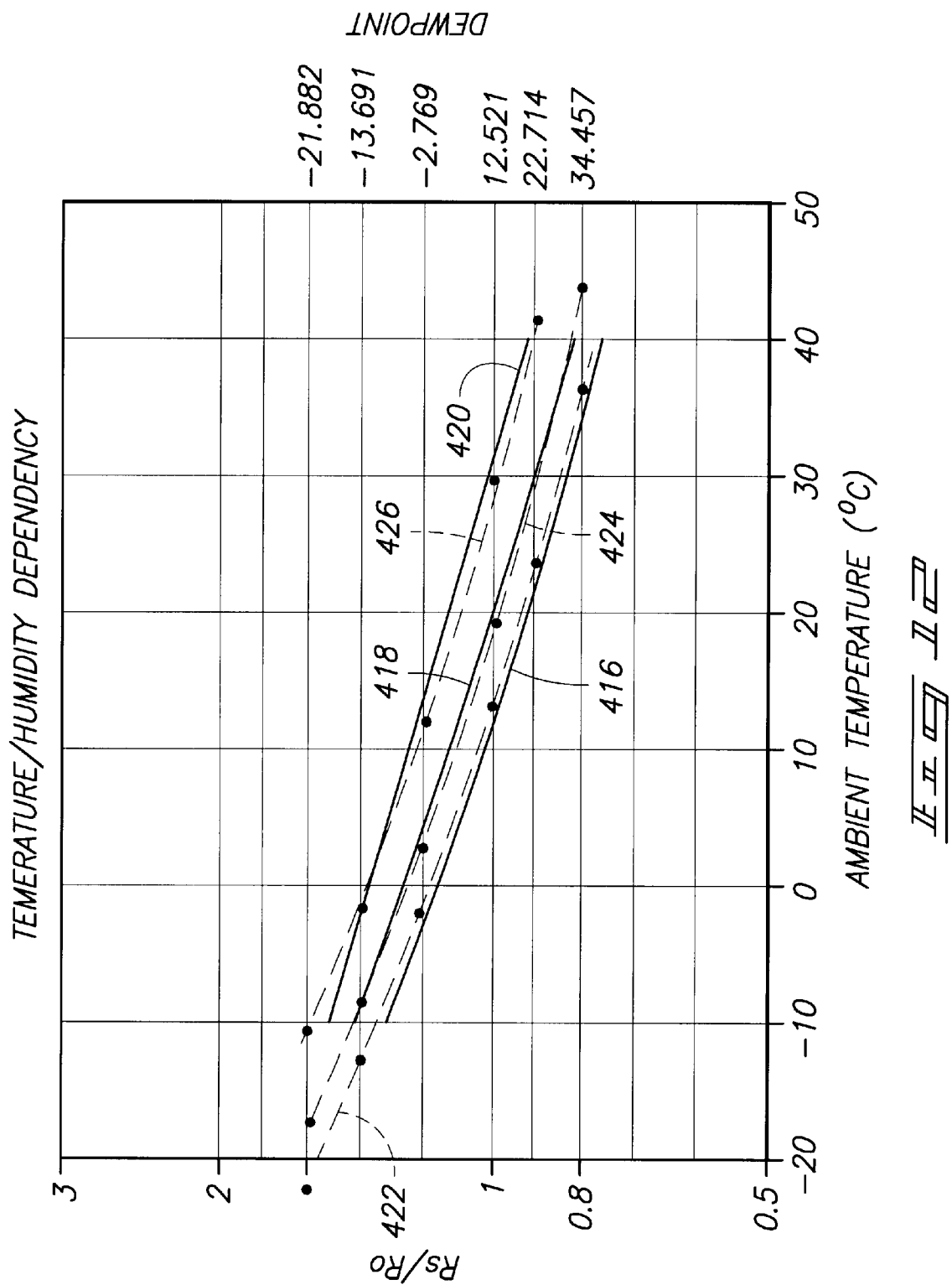
FIG. 12 is a graph illustrating the effects of temperature and humidity on the same MOS gas sensor.

FIG. 12 provides an indication of the conventional way manufacturers of MOS gas sensors look at the effects of temperature and relative humidity. The solid lines 416, 418, and 420 are relative humidities of 95%, 65%, and 35% respectively. FIG. 12 illustrates the conventional view that MOS sensors' Rs/Ro ratios (environmental dependencies) along the y-axis are functions of an infinite number of combinations of relative humidities and ambient temperatures. Therefore, the conventional approach to compensating for environmental dependencies is to use a microprocessor and digital lookup charts to compensate separately for these influences. Besides the disadvantage of basing a critical safety system on a microprocessor and firmware, this method is only an approximation—particularly at lower temperatures and relative humidities.

The environmental uncertainties shown in FIG. 12 are caused by variations in the air's water content as will later be shown in connection with FIGS. 13–15. Manufacturer data includes multiple distinct slopes 416, 418, and 420 of interacting temperatures and relative humidities. Slope 416 indicates temperature/humidity dependency at 95 percent relative humidity, slope 418 indicates temperature/humidity dependency at 65 percent relative humidity, and slope 420 indicates temperature/humidity dependency at 35 percent relative humidity for a particular model sensor, namely the Figaro 821. The FIG. 12 data indicates the sensor's dependencies to temperature and relative humidity according to the manufacturer of same.

Figure 13:
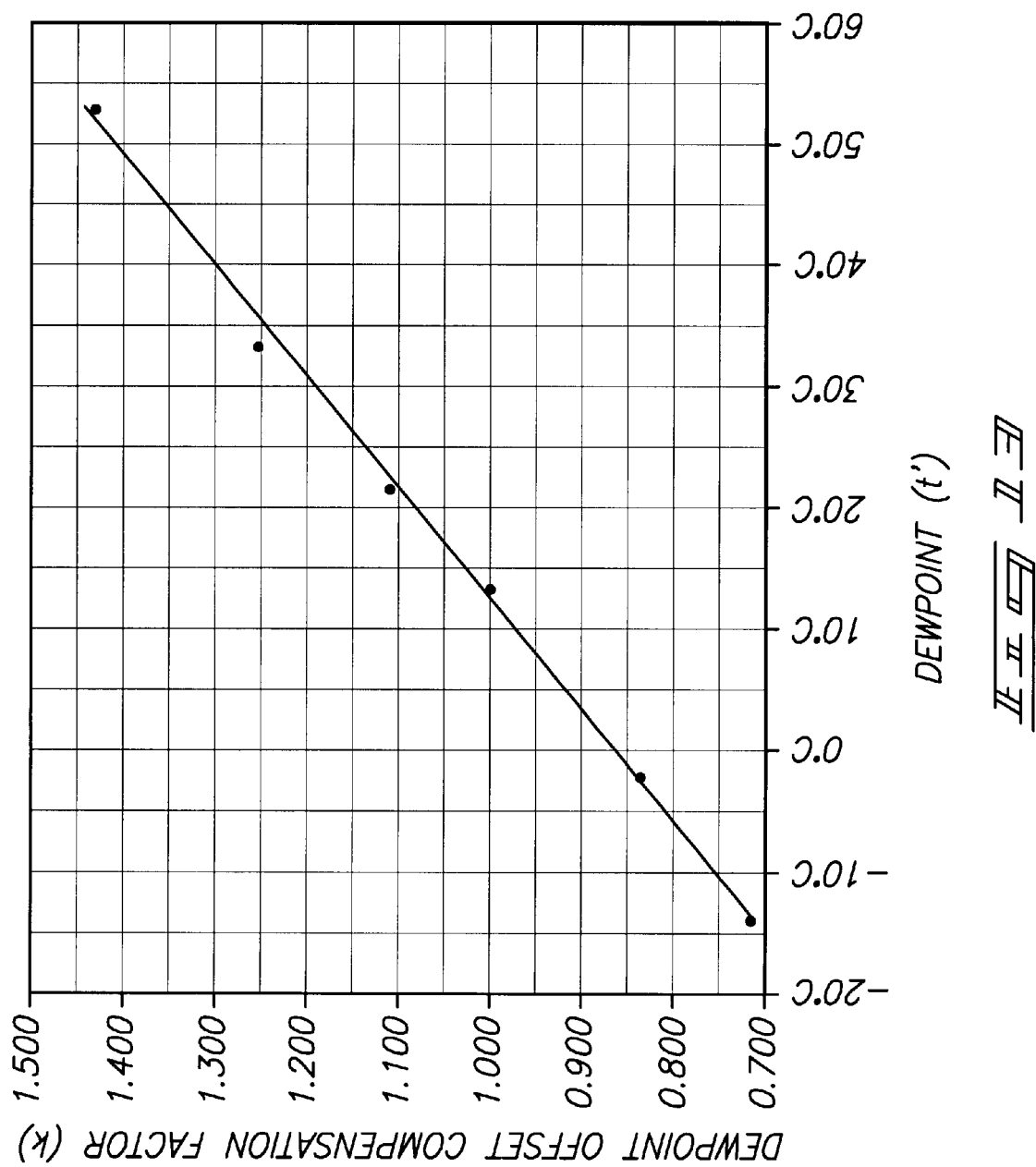
FIG. 13 is a graph illustrating dew points plotted against Rs/Ro values for the same MOS sensor.

FIG. 13 takes the average dew points found at various Rs/Ro values from manufacturer-supplied data of FIG. 12 and plots them against the reciprocal of the Rs/Ro values. As can be seen from FIG. 13, a simple linear function produces an excellent fit to the data points. As seen, the reciprocal of the Rs/Ro values were plotted. If a certain dew point produces an environmental Rs/Ro value of 0.800, an appropriate compensation factor (K) for this model of sensor would be 1.25 (1/0.8).

Referring back to FIG. 12, the dashed slopes 422, 424, and 426 in FIG. 12 are of fixed relative humidity, but they relate dew point (y-axis) to temperature (x-axis). Dashed slopes in FIG. 12 are supplied by applicant, not by the manufacturer of the previously mentioned sensors. The close relationship of these dashed slopes to the manufacturer supplied slopes 416, 418, and 420, that separately consider temperature and relative humidity, can be seen in FIG. 12.

Figure 14:
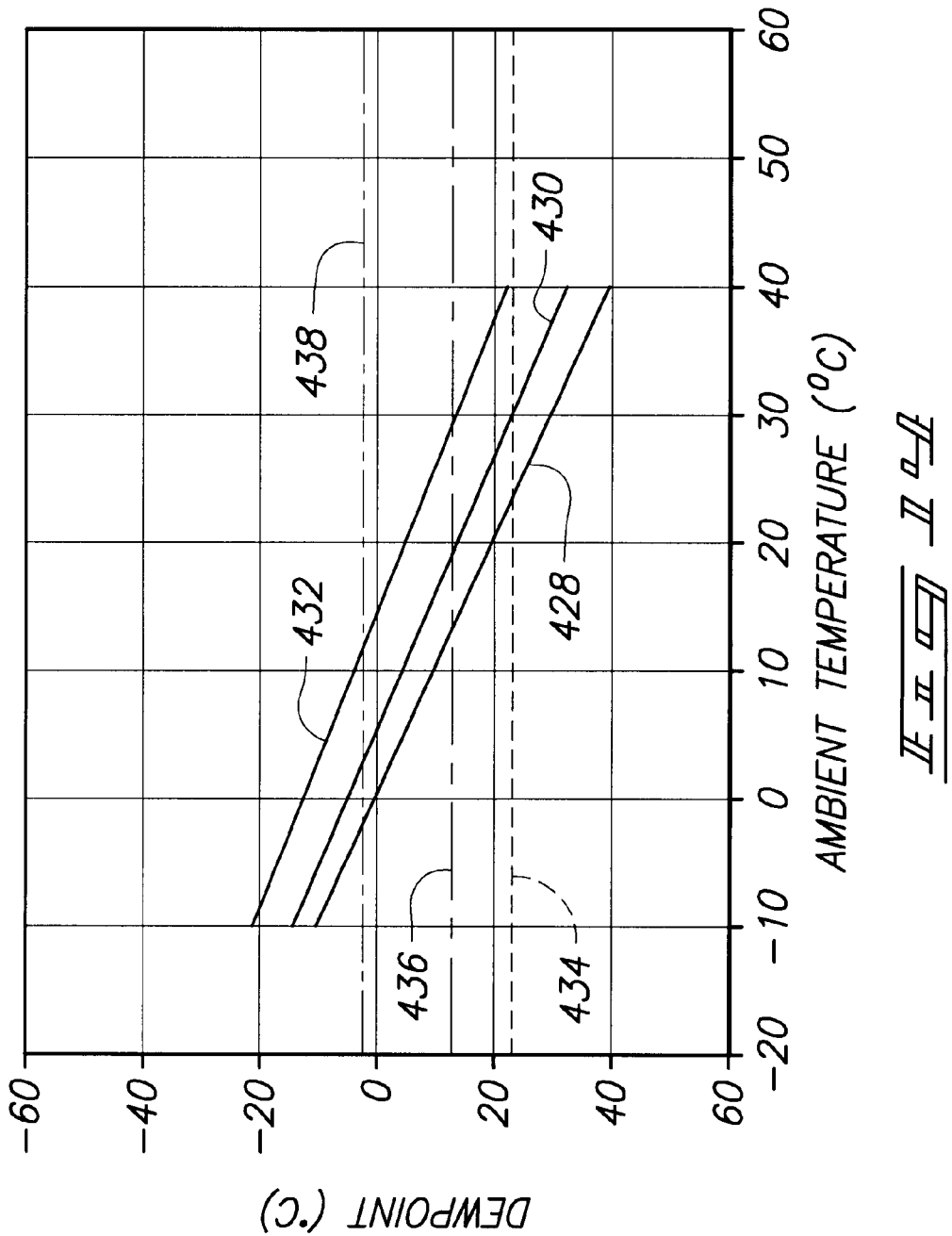
FIG. 14 is a graph illustrating environmental Rs/Ro relationships using dew points for the same MOS gas sensor.

FIG. 14 is a variation of the graph shown in FIG. 12. In FIG. 14, the Rs/Ro ratios on the Y-axis have been replaced with dew points. Slope 428 represents a relative humidity of 95 percent, slope 430 represents a relative humidity of 65 percent, and slope 432 represents a relative humidity of 35 percent. For reference, three of the manufacturer's Rs/Ro ratios—0.9, 1.0, and 1.2—are superimposed over the data. Line 434 represents a Rs/Ro ratio of 0.9, line 436 represents a Rs/Ro of 1.0, and line 438 represents a Rs/Ro of 1.2.

Figure 15:
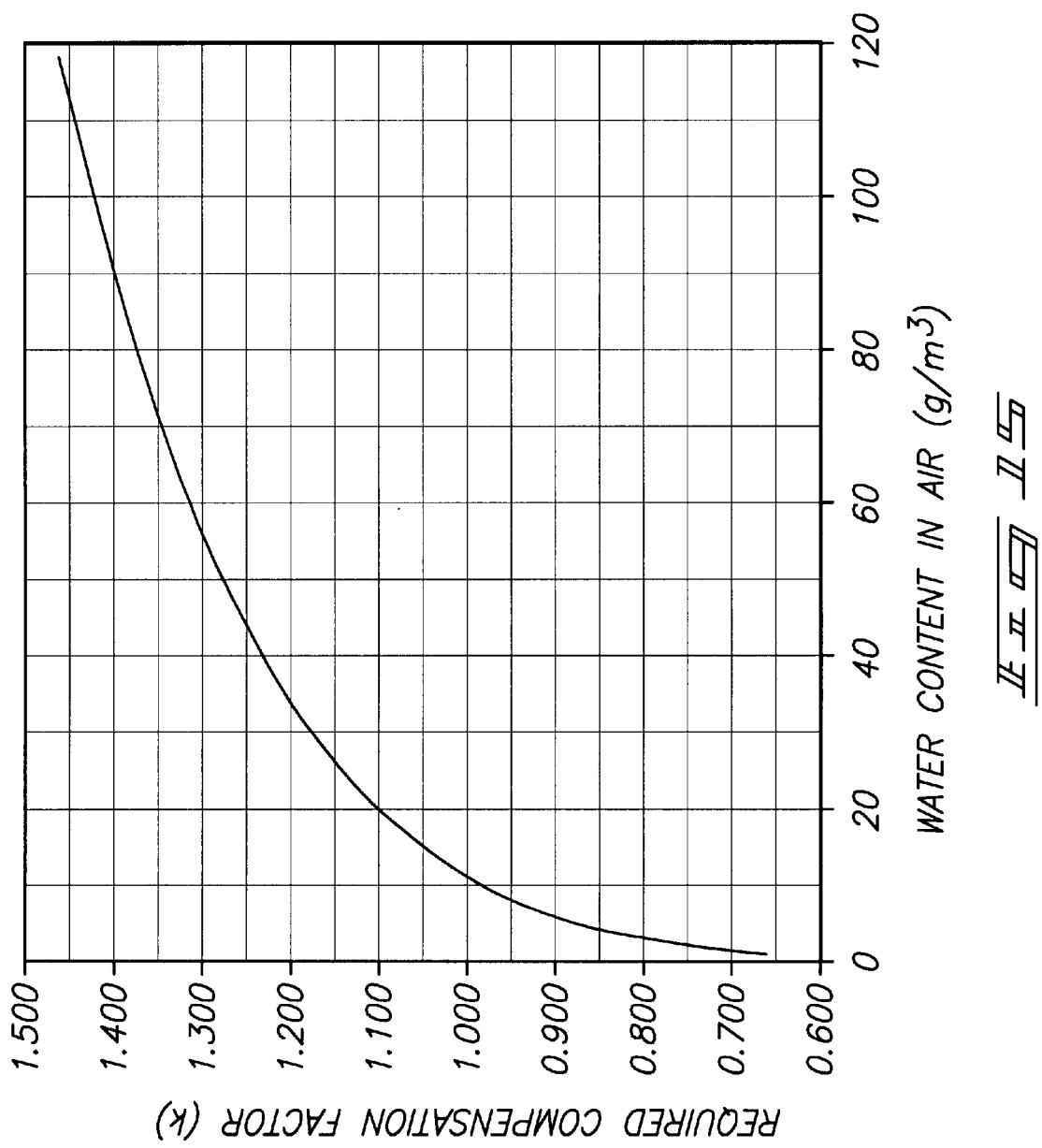
FIG. 15 is a graph illustrating the relationship of compensation factors vs. water content for the same MOS gas sensor.

FIG. 15 shows the relationship of compensation factor vs. mass content of water in air, the industry's metric. When the industry calculates compensation factors, it measures water content in terms of grams per cubic meter. This obscures the relationship between Rs/Ro environmental dependencies and dew point because the relationship to g/m3 produces a nearly straight line only when viewed on a log/linear graph. As shown in FIGS. 13–14, measuring water content in terms of dew point is a much more straightforward endeavor.

Operation

Figure 16:
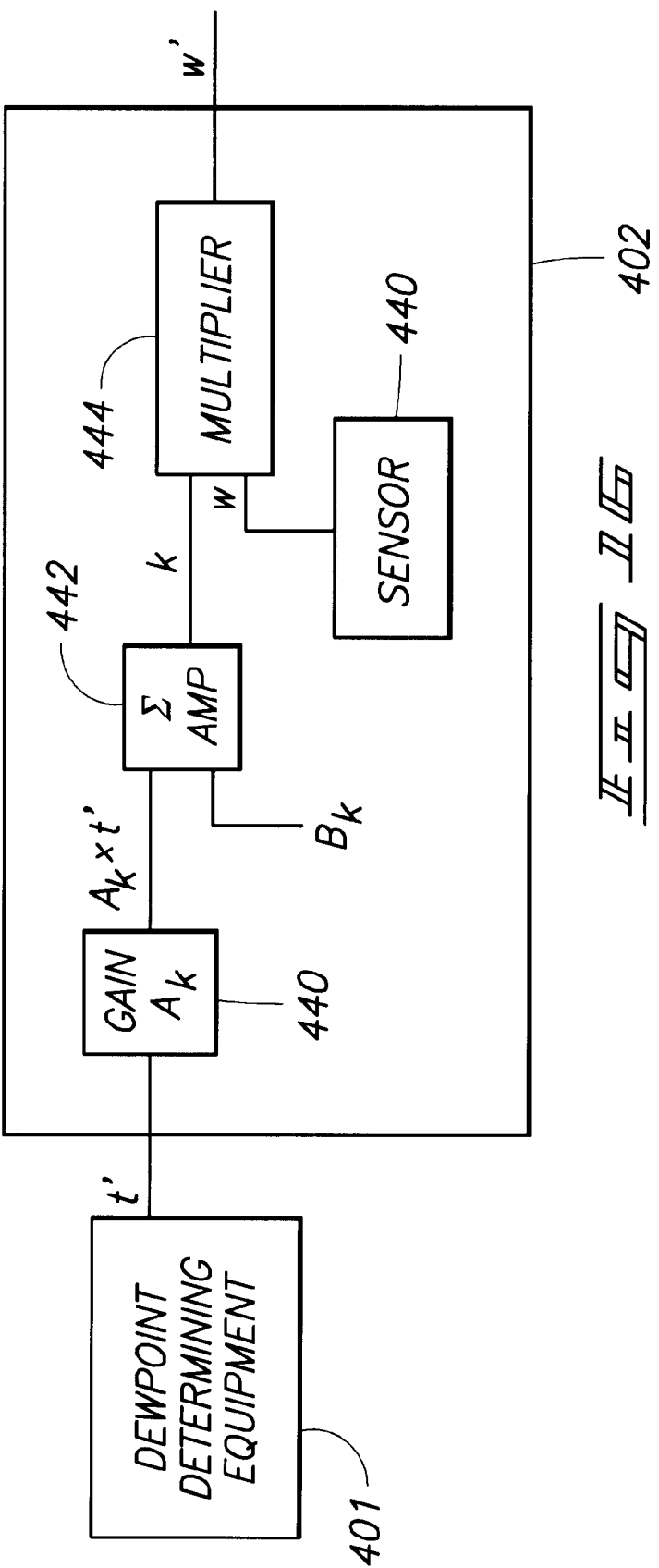
FIG. 16 is a block diagram illustrating the circuitry utilized to transform a dew point signal into a linear or semi-linear compensation factor and multiply that same compensation factor by the output of the MOS gas sensor.

Therefore, in operation, a method of compensating MOS gas sensor 400 comprises using MOS gas sensor 400 to provide a signal indicative of gas concentration of a target gas (e.g., hydrogen) in an ambient (e.g., in the plenum 290); providing a signal representative of dew point of the ambient; and modifying the signal from the MOS gas sensor 400 using the signal representative of dew point to simultaneously compensate for the effects of both temperature and relative humidity. The signal from the gas sensor 400 is modified by the conditioning circuitry 402. In one embodiment, the circuitry 402 comprises analog circuitry. The signal from the gas sensor is modified by the circuitry 402 using the signal representative of dew point by transforming the dew point signal into a linear or semi-linear compensation factor and multiplying that compensation factor by the output of the sensor 400 (see FIG. 16). For one model sensor, the Figaro TGS821 hydrogen sensor, the best fit for sensors with an average $\alpha$ of −0.725 is a simple y=ax+b linear transformation, which is performed as follows: $K=(A_K \times t')+B_K$, where K is the dew point compensation factor ($0.6619 \leq K \leq 1.463$); t' is dew point in °C., $A_K=0.0109$, and $B_K=0.86352$. K is a compensation factor between 0.6619 (−18.5° C. dew point) and 1.463 (55° C. dew point). This range of compensation factors will compensate for environmental Rs/Ro values ranging from 1.511 (the reciprocal of 0.6619) through 0.6835 which is the lowest expected value for the fuel cell system 10 of the illustrated embodiment. In the preferred embodiment, the above-described $A_K$ and $B_K$ coefficients are fixed constants of 0.0109 and 0.86352 respectively and the signal representing the response slope of the sensor (which can range from −0.6 to −1.2) is normalized during calibration to an $\alpha$ of −0.725 before being compensated for the effects of dew point. This is because the magnitude of required change in a particular sensor's signal due to dew point is proportional to the magnitude of its response to hydrogen.

In an alternative embodiment, it is not necessary to normalize the sensor's gain to a specific alpha (such as −0.725) during calibration. This can be accomplished by instead scaling the influence of K factor depending on alpha. For alphas between −1.200 and −0.725, the effect of K factor is accentuated, and for alphas between −0.600 and −0.725, the effect of K factor is attenuated. This is accomplished with the following function: Rcomp=10^(Log(Rs)+(Log(K)/Ka)α). Here, "Rs" is the signal coming from the MOS sensor in terms of resistance (Ω). The term "Ka" is the alpha value at which K factors were optimized for, in this case, where Ak=0.0109 and Bk=0.86352 are the terms used for converting dew point into K factors, Ka=−0.725. The term "α" is the alpha for that particular sensor. The term "Rcomp" is the sensor resistance (Ω) with the effects of environmental dependencies nulled. Hydrogen concentration is then generated with a circuit (or software) that performs the following function: w'=((Log(Rcomp/Ro)+2α)/α). Here, the term w' is the compensated hydrogen concentration (PPM). "Ro" is the resistance (Ω) for that particular sensor at 100 PPM at a K factor of unity. For the TGS821, Ro is typically about 3.2 kΩ but can range from 1.0 kΩ to 10 kΩ.

In still another embodiment, the sensor's α need not be normalized to −0.725 during calibration and its response signal may be directly acted on by the dew point compensating circuitry. In one such embodiment, the coefficients Ak and Bk are not constants and are instead variables that are direct functions of alpha. Alternatively, improved accuracy across the full range of α can be achieved by converting t' into k using a second-order polynomial transformation where the three coefficients Ak, Bk and Ck are variables that are direct functions of alpha. Other alternatives are, of course, possible.

Thus, the circuitry 402 includes (see FIG. 16) an amplifier 440 which, in operation, multiplies t' by $A_k$, a summing amplifier or adder 442 which, in operation, adds that product to $B_k$ to produce the dew point compensation factor K, and a multiplier 444 which, in operation, multiplies the dew point compensation factor K by the output of the sensor 400. In one alternative embodiment, the functionality of the circuitry 402 is implemented in digital circuitry instead of the illustrated analog circuitry. In another alternative embodiment, the functionality of the circuitry 402 is implemented in the controller 250.

Thus, a system has been provided for compensating a gas sensor for the effects of temperature and relative humidity in a simplified fashion.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. A fuel cell power system comprising:
a housing having a fuel gas inlet and an exhaust outlet;
at least one ion exchange membrane fuel cell disposed within the housing; and
a MOS gas sensor system including a MOS gas sensor which, in operation, senses the presence of a fuel in the housing, and which, in operation, provides a signal indicative of the gas concentration of the fuel in the housing;
equipment configured to determine the dew point in the housing; and
compensation circuitry configured to modify the signal from the MOS gas sensor using a compensation factor, which is based upon the determined dew point.

2. A fuel cell system in accordance with claim 1 wherein the compensation circuitry is analog circuitry.

3. A fuel cell system in accordance with claim 1 and further comprising a fuel supply coupled to the fuel supply inlet of the housing and which delivers the fuel.

4. A fuel cell power system in accordance with claim 3 wherein the fuel comprises hydrogen gas, and wherein the MOS sensor of the MOS gas sensor system is configured to sense the concentration of hydrogen gas.

5. A fuel cell power system in accordance with claim 1 wherein the equipment configured to determine the dew point in the housing comprises a temperature sensor which, in operation, generates a signal representative of temperature of the ambient; a relative humidity sensor which, in operation, provides a signal representative of the relative humidity of the ambient; and circuitry, coupled to the analog circuitry, and which, in operation, derives dew point from the temperature and humidity signals.

* * * * *

UNITED STATES PATENT AND TRADEMARK OFFICE
CERTIFICATE OF CORRECTION

PATENT NO. : 6,550,304 B2
DATED : April 22, 2003
INVENTOR(S) : Greg A. Lloyd et al.

It is certified that error appears in the above-identified patent and that said Letters Patent is hereby corrected as shown below:

Column 4,
Line 44, replace "a" with -- $\alpha$ --.

Column 9,
Line 8, replace "Still further, pair" with -- Still further, a pair --.

Column 13,
Line 12, replace "electrically-coupled" with -- electrically coupled --.

Column 14,
Line 29, replace "a" with -- $\alpha$ --.

Column 16,
Line 30, replace "$(0.6619 \leq K \leq 1.463)$"; with -- $(0.6619 \leq K \leq 1.463)$; --.

Column 18,
Line 2, replace "comprising" with -- consisting of --.
Line 6, replace "a MOS" with -- a single MOS --.
Line 14, replace "the MOS" with -- the single MOS --.
Line 22, replace "the MOS" with -- the single MOS --.
Line 23, replace "MOS sensor" with -- MOS gas sensor --.
Line 25, replace "claim 1" with -- claim 3 --.

Signed and Sealed this

Twenty-third Day of September, 2003

JAMES E. ROGAN
*Director of the United States Patent and Trademark Office*

UNITED STATES PATENT AND TRADEMARK OFFICE
CERTIFICATE OF CORRECTION

PATENT NO.     : 6,550,304 B2
DATED          : April 22, 2003
INVENTOR(S)    : Greg A. Lloyd et al.

It is certified that error appears in the above-identified patent and that said Letters Patent is hereby corrected as shown below:

Column 4,
Line 44, replace "a" with -- α --.

Column 9,
Line 3, replace "Still further, pair" with -- Still further, a pair --.

Column 13,
Line 12, replace "electrically-coupled" with -- electrically coupled --.

Column 14,
Line 29, replace "a" with -- α --.

Column 16,
Line 30, replace "($0.6619 \leqq K \leqq 1.463$);" with -- ($0.6619 \leq K \leq 1.463$); --.

Column 18,
Line 2, replace "comprising" with -- consisting of --.
Line 6, replace "a MOS" with -- a single MOS --.
Lines 14 and 22, replace "the MOS" with -- the single MOS --.
Line 23, replace "MOS sensor" with -- MOS gas sensor --.
Line 25, replace "claim 1" with -- claim 3 --.

Signed and Sealed this

Thirteenth Day of April, 2004

JON W. DUDAS
*Acting Director of the United States Patent and Trademark Office*